(12) United States Patent
Kim et al.

(10) Patent No.: US 9,127,257 B2
(45) Date of Patent: Sep. 8, 2015

(54) MODIFIED POLYPEPTIDE HAVING HOMOSERINE ACETYLTRANSFERASE ACTIVITY AND MICROORGANISM EXPRESSING THE SAME

(75) Inventors: So Young Kim, Gyeonggi-do (KR); Yong Uk Shin, Gyeonggi-do (KR); Chang Il Seo, Incheon (KR); In Kyung Heo, Seoul (KR); Ju Eun Kim, Seoul (KR); Hyun Ah Kim, Jeollabuk-do (KR); Han Jin Lee, Seoul (KR); Kwang Ho Na, Seoul (KR); Sung Kwang Son, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 0 days.

(21) Appl. No.: 13/996,990

(22) PCT Filed: Dec. 21, 2011

(86) PCT No.: PCT/KR2011/009966
§ 371 (c)(1),
(2), (4) Date: Jun. 21, 2013

(87) PCT Pub. No.: WO2012/087039
PCT Pub. Date: Jun. 28, 2012

(65) Prior Publication Data
US 2013/0273615 A1    Oct. 17, 2013

(30) Foreign Application Priority Data

Dec. 21, 2010 (KR) .......................... 10-2010-0131953
Dec. 21, 2011 (KR) .......................... 10-2011-0139228

(51) Int. Cl.
C12N 9/10      (2006.01)
C12N 15/70     (2006.01)
(Continued)

(52) U.S. Cl.
CPC ............... *C12N 9/1029* (2013.01); *C12N 1/00* (2013.01); *C12N 15/70* (2013.01); *C12N 15/74* (2013.01); *C12P 13/06* (2013.01); *C12Y 203/01031* (2013.01)

(58) Field of Classification Search
None
See application file for complete search history.

(56) References Cited

U.S. PATENT DOCUMENTS 7,195,897 B2    3/2007  Leonhartsberger et al.
7,238,502 B2 *  7/2007  Kroger et al. ............... 435/113
(Continued)

FOREIGN PATENT DOCUMENTS

CN    101688190 A    3/2010
JP    2009-060791    3/2009
(Continued)

OTHER PUBLICATIONS

Zubieta et al., "A single amino acid change is responsible for evolution of acyltransferase specificity in bacterial methionine biosythesis", Journal of Biological Chemistry, vol. 283, No. 12, pp. 7561-7567, 2008.*

(Continued)

*Primary Examiner* — Rebecca Prouty
*Assistant Examiner* — Richard Ekstrom
(74) *Attorney, Agent, or Firm* — Seed IP Law Group PLLC

(57) ABSTRACT

The present invention relates to a polypeptide that is modified to have homoserine O-acetyltransferase activity, and in particular, the present invention provides a modified polypeptide having homoserine O-acetyltransferase activity, in which the amino acid at position 111 of a polypeptide having homoserine succinyltransferase activity is substituted with other amino acid.

23 Claims, 8 Drawing Sheets

(51) Int. Cl.
*C12N 15/74* (2006.01)
*C12N 1/00* (2006.01)
*C12P 13/06* (2006.01)

(56) References Cited

U.S. PATENT DOCUMENTS

| | | | |
|---|---|---|---|
| 7,611,873 | B1 | 11/2009 | Usuda et al. |
| 7,851,180 | B2 | 12/2010 | Shin et al. |
| 2004/0199941 | A1* | 10/2004 | San et al. ............... 800/281 |
| 2009/0253187 | A1* | 10/2009 | Shin et al. ............... 435/116 |
| 2011/0053252 | A1* | 3/2011 | Kim et al. ............ 435/252.33 |
| 2011/0053253 | A1* | 3/2011 | Kim et al. ............ 435/252.33 |
| 2011/0183383 | A1* | 7/2011 | Brazeau et al. ........... 435/113 |
| 2011/0207184 | A1* | 8/2011 | Kim et al. ............... 435/113 |

FOREIGN PATENT DOCUMENTS

| | | |
|---|---|---|
| JP | 2009-247354 | 10/2009 |
| JP | 2010-523145 | 7/2010 |
| KR | 10-2009-0106365 A | 10/2009 |
| WO | 2004/076659 A2 | 9/2004 |
| WO | 2004/108894 A2 | 12/2004 |
| WO | WO 2007116955 A2 * | 10/2007 |
| WO | 2008/127240 A1 | 10/2008 |

OTHER PUBLICATIONS

GenBank Accession No. YP_002228775.1, published 2008.*
GenBank Accession No. NP_981826.1, published 2004.*
GenBank Accession No. AM933173.1, published 2008.*
Rock et al., "Role of feedback regulation of pantothenate kinase (CoaA) in control of coenzyme A levels of *Escherichia coli*", Journal of Bacteriology, vol. 185, No. 11, pp. 3410-3415, 2003.*
International Search Report, dated Jun. 20, 2012, for International Application No. PCT/KR2011/009966, 6 pages.
NCBI Reference Sequence NP_418437.1, "homoserine O-transsuccinylase [*Escherichia coli* str. K-12 substr. MG1655]," retrieved Jun. 20, 2013, 3 pages.
Chinese Office Action issued on Feb. 25, 2015, corresponding to copending Chinese Application No. 201180065592.X (19 pages with translation).
Zubieta et al., "Supplemental Data—Table Three: Summary of species and acyltransferase types," 283(12):18-18 (2008), Journal of Biological Chemistry.
Supplemental European Search Report corresponding to copending EP Application No. 11 85 2010, dated Jan. 19, 2015 (7 pages).

* cited by examiner

SEQUENCE LISTING

```
<160> NUMBER OF SEQ ID NOS: 51

<210> SEQ ID NO 1
<211> LENGTH: 29
<212> TYPE: DNA
<213> ORGANISM: Artificial Sequence
<220> FEATURE:
<223> OTHER INFORMATION: Forward primer

<400> SEQUENCE: 1
aattgatatc atgccgattc gtgtgccgg                                      29

<210> SEQ ID NO 2
<211> LENGTH: 34
<212> TYPE: DNA
<213> ORGANISM: Artificial Sequence
<220> FEATURE:
<223> OTHER INFORMATION: Reverse primer

<400> SEQUENCE: 2
aattaagctt ttaatccagc gttggattca tgtg                                34

<210> SEQ ID NO 3
<211> LENGTH: 27
<212> TYPE: DNA
<213> ORGANISM: Artificial Sequence
<220> FEATURE:
<223> OTHER INFORMATION: Forward primer

<400> SEQUENCE: 3
aattgatatc atgaccgccg tgctcgc                                        27

<210> SEQ ID NO 4
<211> LENGTH: 31
<212> TYPE: DNA
<213> ORGANISM: Artificial Sequence
<220> FEATURE:
<223> OTHER INFORMATION: Reverse  primer

<400> SEQUENCE: 4
aattaagctt tcaactcctg agaaacgccc c                                   31

<210> SEQ ID NO 5
<211> LENGTH: 44
<212> TYPE: DNA
<213> ORGANISM: Artificial Sequence
<220> FEATURE:
<223> OTHER INFORMATION: Forward  primer

<400> SEQUENCE: 5
ttgtaactgg tgcgccgctg gaactggtgg ggtttaatga tgtc                     44
```

```
<210> SEQ ID NO 6
<211> LENGTH: 44
<212> TYPE: DNA
<213> ORGANISM: Artificial Sequence
<220> FEATURE:
<223> OTHER INFORMATION: Reverse primer

<400> SEQUENCE: 6
gacatcatta aaccccacca gttccagcgg cgcaccagtt acaa            44

<210> SEQ ID NO 7
<211> LENGTH: 44
<212> TYPE: DNA
<213> ORGANISM: Artificial Sequence
<220> FEATURE:
<223> OTHER INFORMATION: Forward primer

<400> SEQUENCE: 7
tgtaactggt gcgccgctgg aaaccgtggg gtttaatgat gtcg            44

<210> SEQ ID NO 8
<211> LENGTH: 44
<212> TYPE: DNA
<213> ORGANISM: Artificial Sequence
<220> FEATURE:
<223> OTHER INFORMATION: Reverse primer

<400> SEQUENCE: 8
cgacatcatt aaccccacg gtttccagcg gcgcaccagt taca             44

<210> SEQ ID NO 9
<211> LENGTH: 44
<212> TYPE: DNA
<213> ORGANISM: Artificial Sequence
<220> FEATURE:
<223> OTHER INFORMATION: Forward primer

<400> SEQUENCE: 9
tgtaactggt gcgccgctgg aacatgtggg gtttaatgat gtcg            44

<210> SEQ ID NO 10
<211> LENGTH: 44
<212> TYPE: DNA
<213> ORGANISM: Artificial Sequence
<220> FEATURE:
<223> OTHER INFORMATION: Reverse primer

<400> SEQUENCE: 10
cgacatcatt aaccccaca tgttccagcg gcgcaccagt taca             44

<210> SEQ ID NO 11
<211> LENGTH: 35
<212> TYPE: DNA
<213> ORGANISM: Artificial Sequence
<220> FEATURE:
<223> OTHER INFORMATION: Forward primer

<400> SEQUENCE: 11
atgacaactt ctcgtgcgcc tggtcaggaa attcg                      35

<210> SEQ ID NO 12
<211> LENGTH: 35
<212> TYPE: DNA
<213> ORGANISM: Artificial Sequence
<220> FEATURE:
```

<223> OTHER INFORMATION: Reverse primer

<400> SEQUENCE: 12
cgaatttcct gaccaggcgc acgagaagtt gtcat     35

<210> SEQ ID NO 13
<211> LENGTH: 35
<212> TYPE: DNA
<213> ORGANISM: Artificial Sequence
<220> FEATURE:
<223> OTHER INFORMATION: Forward primer

<400> SEQUENCE: 13
cgccgctggg cctggtgggg tttaatgatg tcgct     35

<210> SEQ ID NO 14
<211> LENGTH: 35
<212> TYPE: DNA
<213> ORGANISM: Artificial Sequence
<220> FEATURE:
<223> OTHER INFORMATION: Reverse primer

<400> SEQUENCE: 14
agcgacatca ttaaacccca ccaggcccag cggcg     35

<210> SEQ ID NO 15
<211> LENGTH: 35
<212> TYPE: DNA
<213> ORGANISM: Artificial Sequence
<220> FEATURE:
<223> OTHER INFORMATION: Forward primer

<400> SEQUENCE: 15
cacgtcacct cgacgctgag tgtctgctgg gcggt     35

<210> SEQ ID NO 16
<211> LENGTH: 35
<212> TYPE: DNA
<213> ORGANISM: Artificial Sequence
<220> FEATURE:
<223> OTHER INFORMATION: Reverse primer

<400> SEQUENCE: 16
accgcccagc agacactcag cgtcgaggtg acgtg     35

<210> SEQ ID NO 17
<211> LENGTH: 309
<212> TYPE: PRT
<213> ORGANISM: Artificial Sequence
<220> FEATURE:
<223> OTHER INFORMATION: MetA polypeptide having homoserine O-succinyl
      transferase
      activity

<400> SEQUENCE: 17

Met Pro Ile Arg Val Pro Asp Glu Leu Pro Ala Val Asn Phe Leu Arg
 1               5                  10                  15

Glu Glu Asn Val Phe Val Met Thr Thr Ser Arg Ala Ser Gly Gln Glu
                20                  25                  30

Ile Arg Pro Leu Lys Val Leu Ile Leu Asn Leu Met Pro Lys Lys Ile
            35                  40                  45

Glu Thr Glu Asn Gln Phe Leu Arg Leu Leu Ser Asn Ser Pro Leu Gln
        50                  55                  60

Val Asp Ile Gln Leu Leu Arg Ile Asp Ser Arg Glu Ser Arg Asn Thr

Pro Ala Glu His Leu Asn Asn Phe Tyr Cys Asn Phe Glu Asp Ile Gln
            85                  90                  95

Asp Gln Asn Phe Asp Gly Leu Ile Val Thr Gly Ala Pro Leu Gly Leu
            100                 105                 110

Val Glu Phe Asn Asp Val Ala Tyr Trp Pro Gln Ile Lys Gln Val Leu
            115                 120                 125

Glu Trp Ser Lys Asp His Val Thr Ser Thr Leu Phe Val Cys Trp Ala
        130                 135                 140

Val Gln Ala Ala Leu Asn Ile Leu Tyr Gly Ile Pro Lys Gln Thr Arg
145                 150                 155                 160

Thr Glu Lys Leu Ser Gly Val Tyr Glu His His Ile Leu His Pro His
                165                 170                 175

Ala Leu Leu Thr Arg Gly Phe Asp Asp Ser Phe Leu Ala Pro His Ser
            180                 185                 190

Arg Tyr Ala Asp Phe Pro Ala Ala Leu Ile Arg Asp Tyr Thr Asp Leu
            195                 200                 205

Glu Ile Leu Ala Glu Thr Glu Glu Gly Asp Ala Tyr Leu Phe Ala Ser
        210                 215                 220

Lys Asp Lys Arg Ile Ala Phe Val Thr Gly His Pro Glu Tyr Asp Ala
225                 230                 235                 240

Gln Thr Leu Ala Gln Glu Phe Phe Arg Asp Val Glu Ala Gly Leu Asp
                245                 250                 255

Pro Asp Val Pro Tyr Asn Tyr Phe Pro His Asn Asp Pro Gln Asn Thr
            260                 265                 270

Pro Arg Ala Ser Trp Arg Ser His Gly Asn Leu Leu Phe Thr Asn Trp
            275                 280                 285

Leu Asn Tyr Tyr Val Tyr Gln Ile Thr Pro Tyr Asp Leu Arg His Met
        290                 295                 300

Asn Pro Thr Leu Asp
305

<210> SEQ ID NO 18
<211> LENGTH: 309
<212> TYPE: PRT
<213> ORGANISM: Artificial Sequence
<220> FEATURE:
<223> OTHER INFORMATION: Variant polypeptide having homoserine O-acetyl
      transferase
      activity metA EL

<400> SEQUENCE: 18

Met Pro Ile Arg Val Pro Asp Glu Leu Pro Ala Val Asn Phe Leu Arg
 1               5                  10                  15

Glu Glu Asn Val Phe Val Met Thr Thr Ser Arg Ala Ser Gly Gln Glu
            20                  25                  30

Ile Arg Pro Leu Lys Val Leu Ile Leu Asn Leu Met Pro Lys Lys Ile
        35                  40                  45

Glu Thr Glu Asn Gln Phe Leu Arg Leu Leu Ser Asn Ser Pro Leu Gln
    50                  55                  60

Val Asp Ile Gln Leu Leu Arg Ile Asp Ser Arg Glu Ser Arg Asn Thr
65                  70                  75                  80

Pro Ala Glu His Leu Asn Asn Phe Tyr Cys Asn Phe Glu Asp Ile Gln
            85                  90                  95

Asp Gln Asn Phe Asp Gly Leu Ile Val Thr Gly Ala Pro Leu Glu Leu
            100                 105                 110

```
Val Glu Phe Asn Asp Val Ala Tyr Trp Pro Gln Ile Lys Gln Val Leu
            115                 120                 125

Glu Trp Ser Lys Asp His Val Thr Ser Thr Leu Phe Val Cys Trp Ala
        130                 135                 140

Val Gln Ala Ala Leu Asn Ile Leu Tyr Gly Ile Pro Lys Gln Thr Arg
145                 150                 155                 160

Thr Glu Lys Leu Ser Gly Val Tyr Glu His His Ile Leu His Pro His
                165                 170                 175

Ala Leu Leu Thr Arg Gly Phe Asp Asp Ser Phe Leu Ala Pro His Ser
            180                 185                 190

Arg Tyr Ala Asp Phe Pro Ala Ala Leu Ile Arg Asp Tyr Thr Asp Leu
        195                 200                 205

Glu Ile Leu Ala Glu Thr Glu Glu Gly Asp Ala Tyr Leu Phe Ala Ser
210                 215                 220

Lys Asp Lys Arg Ile Ala Phe Val Thr Gly His Pro Glu Tyr Asp Ala
225                 230                 235                 240

Gln Thr Leu Ala Gln Glu Phe Phe Arg Asp Val Glu Ala Gly Leu Asp
                245                 250                 255

Pro Asp Val Pro Tyr Asn Tyr Phe Pro His Asn Asp Pro Gln Asn Thr
            260                 265                 270

Pro Arg Ala Ser Trp Arg Ser His Gly Asn Leu Leu Phe Thr Asn Trp
        275                 280                 285

Leu Asn Tyr Tyr Val Tyr Gln Ile Thr Pro Tyr Asp Leu Arg His Met
290                 295                 300

Asn Pro Thr Leu Asp
305

<210> SEQ ID NO 19
<211> LENGTH: 309
<212> TYPE: PRT
<213> ORGANISM: Artificial Sequence
<220> FEATURE:
<223> OTHER INFORMATION: Variant polypeptide having homoserine O-acetyl
      transferase
      activity metA ET

<400> SEQUENCE: 19

Met Pro Ile Arg Val Pro Asp Glu Leu Pro Ala Val Asn Phe Leu Arg
  1               5                  10                  15

Glu Glu Asn Val Phe Val Met Thr Thr Ser Arg Ala Ser Gly Gln Glu
                 20                  25                  30

Ile Arg Pro Leu Lys Val Leu Ile Leu Asn Leu Met Pro Lys Lys Ile
            35                  40                  45

Glu Thr Glu Asn Gln Phe Leu Arg Leu Ser Asn Ser Pro Leu Gln
    50                  55                  60

Val Asp Ile Gln Leu Leu Arg Ile Asp Ser Arg Glu Ser Arg Asn Thr
65                  70                  75                  80

Pro Ala Glu His Leu Asn Asn Phe Tyr Cys Asn Phe Glu Asp Ile Gln
                85                  90                  95

Asp Gln Asn Phe Asp Gly Leu Ile Val Thr Gly Ala Pro Leu Glu Thr
            100                 105                 110

Val Glu Phe Asn Asp Val Ala Tyr Trp Pro Gln Ile Lys Gln Val Leu
            115                 120                 125

Glu Trp Ser Lys Asp His Val Thr Ser Thr Leu Phe Val Cys Trp Ala
        130                 135                 140
```

```
Val Gln Ala Ala Leu Asn Ile Leu Tyr Gly Ile Pro Lys Gln Thr Arg
145                 150                 155                 160

Thr Glu Lys Leu Ser Gly Val Tyr Glu His His Ile Leu His Pro His
                165                 170                 175

Ala Leu Leu Thr Arg Gly Phe Asp Asp Ser Phe Leu Ala Pro His Ser
            180                 185                 190

Arg Tyr Ala Asp Phe Pro Ala Ala Leu Ile Arg Asp Tyr Thr Asp Leu
        195                 200                 205

Glu Ile Leu Ala Glu Thr Glu Gly Asp Ala Tyr Leu Phe Ala Ser
    210                 215                 220

Lys Asp Lys Arg Ile Ala Phe Val Thr Gly His Pro Glu Tyr Asp Ala
225                 230                 235                 240

Gln Thr Leu Ala Gln Glu Phe Phe Arg Asp Val Glu Ala Gly Leu Asp
                245                 250                 255

Pro Asp Val Pro Tyr Asn Tyr Phe Pro His Asn Asp Pro Gln Asn Thr
            260                 265                 270

Pro Arg Ala Ser Trp Arg Ser His Gly Asn Leu Leu Phe Thr Asn Trp
        275                 280                 285

Leu Asn Tyr Tyr Val Tyr Gln Ile Thr Pro Tyr Asp Leu Arg His Met
    290                 295                 300

Asn Pro Thr Leu Asp
305

<210> SEQ ID NO 20
<211> LENGTH: 309
<212> TYPE: PRT
<213> ORGANISM: Artificial Sequence
<220> FEATURE:
<223> OTHER INFORMATION: Variant polypeptide having homoserine O-acetyl
      transferase
      activity metA EH

<400> SEQUENCE: 20

Met Pro Ile Arg Val Pro Asp Glu Leu Pro Ala Val Asn Phe Leu Arg
1               5                   10                  15

Glu Glu Asn Val Phe Val Met Thr Thr Ser Arg Ala Ser Gly Gln Glu
                20                  25                  30

Ile Arg Pro Leu Lys Val Leu Ile Leu Asn Leu Met Pro Lys Lys Ile
            35                  40                  45

Glu Thr Glu Asn Gln Phe Leu Arg Leu Leu Ser Asn Ser Pro Leu Gln
        50                  55                  60

Val Asp Ile Gln Leu Leu Arg Ile Asp Ser Arg Glu Ser Arg Asn Thr
65                  70                  75                  80

Pro Ala Glu His Leu Asn Asn Phe Tyr Cys Asn Phe Glu Asp Ile Gln
                85                  90                  95

Asp Gln Asn Phe Asp Gly Leu Ile Val Thr Gly Ala Pro Leu Glu His
            100                 105                 110

Val Glu Phe Asn Asp Val Ala Tyr Trp Pro Gln Ile Lys Gln Val Leu
        115                 120                 125

Glu Trp Ser Lys Asp His Val Thr Ser Thr Leu Phe Val Cys Trp Ala
130                 135                 140

Val Gln Ala Ala Leu Asn Ile Leu Tyr Gly Ile Pro Lys Gln Thr Arg
145                 150                 155                 160

Thr Glu Lys Leu Ser Gly Val Tyr Glu His His Ile Leu His Pro His
                165                 170                 175

Ala Leu Leu Thr Arg Gly Phe Asp Asp Ser Phe Leu Ala Pro His Ser
```

```
                180                 185                 190
Arg Tyr Ala Asp Phe Pro Ala Ala Leu Ile Arg Asp Tyr Thr Asp Leu
            195                 200                 205

Glu Ile Leu Ala Glu Thr Glu Glu Gly Asp Ala Tyr Leu Phe Ala Ser
    210                 215                 220

Lys Asp Lys Arg Ile Ala Phe Val Thr Gly His Pro Glu Tyr Asp Ala
225                 230                 235                 240

Gln Thr Leu Ala Gln Glu Phe Phe Arg Asp Val Glu Ala Gly Leu Asp
                245                 250                 255

Pro Asp Val Pro Tyr Asn Tyr Phe Pro His Asn Asp Pro Gln Asn Thr
            260                 265                 270

Pro Arg Ala Ser Trp Arg Ser His Gly Asn Leu Leu Phe Thr Asn Trp
        275                 280                 285

Leu Asn Tyr Tyr Val Tyr Gln Ile Thr Pro Tyr Asp Leu Arg His Met
    290                 295                 300

Asn Pro Thr Leu Asp
305

<210> SEQ ID NO 21
<211> LENGTH: 309
<212> TYPE: PRT
<213> ORGANISM: Artificial Sequence
<220> FEATURE:
<223> OTHER INFORMATION: feedback-resistance variant polypeptide having
      hoserine
      O-acetyl transferase activity met11A EL

<400> SEQUENCE: 21

Met Pro Ile Arg Val Pro Asp Glu Leu Pro Ala Val Asn Phe Leu Arg
  1               5                  10                  15

Glu Glu Asn Val Phe Val Met Thr Thr Ser Arg Ala Pro Gly Gln Glu
                 20                  25                  30

Ile Arg Pro Leu Lys Val Leu Ile Leu Asn Leu Met Pro Lys Lys Ile
             35                  40                  45

Glu Thr Glu Asn Gln Phe Leu Arg Leu Leu Ser Asn Ser Pro Leu Gln
         50                  55                  60

Val Asp Ile Gln Leu Leu Arg Ile Asp Ser Arg Glu Ser Arg Asn Thr
65                  70                  75                  80

Pro Ala Glu His Leu Asn Asn Phe Tyr Cys Asn Phe Glu Asp Ile Gln
                 85                  90                  95

Asp Gln Asn Phe Asp Glu Thr Ile Val Thr Gly Ala Pro Leu Glu Leu
            100                 105                 110

Val Gly Phe Asn Asp Val Ala Tyr Trp Pro Gln Ile Lys Gln Val Leu
        115                 120                 125

Glu Trp Ser Lys Asp His Val Thr Ser Thr Leu Ser Val Cys Trp Ala
    130                 135                 140

Val Gln Ala Ala Leu Asn Ile Leu Tyr Gly Ile Pro Lys Gln Thr Arg
145                 150                 155                 160

Thr Glu Lys Leu Ser Gly Val Tyr Glu His His Ile Leu His Pro His
                165                 170                 175

Ala Leu Leu Thr Arg Gly Phe Asp Asp Ser Phe Leu Ala Pro His Ser
            180                 185                 190

Arg Tyr Ala Asp Phe Pro Ala Ala Leu Ile Arg Asp Tyr Thr Asp Leu
        195                 200                 205

Glu Ile Leu Ala Glu Thr Glu Glu Gly Asp Ala Tyr Leu Phe Ala Ser
    210                 215                 220
```

```
Lys Asp Lys Arg Ile Ala Phe Val Thr Gly His Pro Glu Tyr Asp Ala
225                 230                 235                 240

Gln Thr Leu Ala Gln Glu Phe Phe Arg Asp Val Glu Ala Gly Leu Asp
                245                 250                 255

Pro Asp Val Pro Tyr Asn Tyr Phe Pro His Asn Asp Pro Gln Asn Thr
            260                 265                 270

Pro Arg Ala Ser Trp Arg Ser His Gly Asn Leu Leu Phe Thr Asn Trp
        275                 280                 285

Leu Asn Tyr Tyr Val Tyr Gln Ile Thr Pro Tyr Asp Leu Arg His Met
    290                 295                 300

Asn Pro Thr Leu Asp
305

<210> SEQ ID NO 22
<211> LENGTH: 309
<212> TYPE: PRT
<213> ORGANISM: Artificial Sequence
<220> FEATURE:
<223> OTHER INFORMATION: feedback-resistance variant polypeptide having
      hoserine
      O-acetyl transferase activity met11A ET

<400> SEQUENCE: 22

Met Pro Ile Arg Val Pro Asp Glu Leu Pro Ala Val Asn Phe Leu Arg
  1               5                  10                  15

Glu Glu Asn Val Phe Val Met Thr Thr Ser Arg Ala Pro Gly Gln Glu
                 20                  25                  30

Ile Arg Pro Leu Lys Val Leu Ile Leu Asn Leu Met Pro Lys Lys Ile
             35                  40                  45

Glu Thr Glu Asn Gln Phe Leu Arg Leu Ser Asn Ser Pro Leu Gln
     50                  55                  60

Val Asp Ile Gln Leu Leu Arg Ile Asp Ser Arg Glu Ser Arg Asn Thr
 65                  70                  75                  80

Pro Ala Glu His Leu Asn Asn Phe Tyr Cys Asn Phe Glu Asp Ile Gln
                 85                  90                  95

Asp Gln Asn Phe Asp Glu Thr Ile Val Thr Gly Ala Pro Leu Glu Thr
                100                 105                 110

Val Gly Phe Asn Asp Val Ala Tyr Trp Pro Gln Ile Lys Gln Val Leu
            115                 120                 125

Glu Trp Ser Lys Asp His Val Thr Ser Thr Leu Ser Val Cys Trp Ala
        130                 135                 140

Val Gln Ala Ala Leu Asn Ile Leu Tyr Gly Ile Pro Lys Gln Thr Arg
145                 150                 155                 160

Thr Glu Lys Leu Ser Gly Val Tyr Glu His His Ile Leu His Pro His
                165                 170                 175

Ala Leu Leu Thr Arg Gly Phe Asp Asp Ser Phe Leu Ala Pro His Ser
            180                 185                 190

Arg Tyr Ala Asp Phe Pro Ala Ala Leu Ile Arg Asp Tyr Thr Asp Leu
        195                 200                 205

Glu Ile Leu Ala Glu Thr Glu Glu Gly Asp Ala Tyr Leu Phe Ala Ser
    210                 215                 220

Lys Asp Lys Arg Ile Ala Phe Val Thr Gly His Pro Glu Tyr Asp Ala
225                 230                 235                 240

Gln Thr Leu Ala Gln Glu Phe Phe Arg Asp Val Glu Ala Gly Leu Asp
                245                 250                 255
```

Pro Asp Val Pro Tyr Asn Tyr Phe Pro His Asn Asp Pro Gln Asn Thr
            260                 265                 270

Pro Arg Ala Ser Trp Arg Ser His Gly Asn Leu Leu Phe Thr Asn Trp
        275                 280                 285

Leu Asn Tyr Tyr Val Tyr Gln Ile Thr Pro Tyr Asp Leu Arg His Met
        290                 295                 300

Asn Pro Thr Leu Asp
305

<210> SEQ ID NO 23
<211> LENGTH: 309
<212> TYPE: PRT
<213> ORGANISM: Artificial Sequence
<220> FEATURE:
<223> OTHER INFORMATION: feedback-resistance variant polypeptide having
      hoserine
      O-acetyl transferase activity met11A EH

<400> SEQUENCE: 23

Met Pro Ile Arg Val Pro Asp Glu Leu Pro Ala Val Asn Phe Leu Arg
  1               5                  10                  15

Glu Glu Asn Val Phe Val Met Thr Thr Ser Arg Ala Pro Gly Gln Glu
            20                  25                  30

Ile Arg Pro Leu Lys Val Leu Ile Leu Asn Leu Met Pro Lys Lys Ile
        35                  40                  45

Glu Thr Glu Asn Gln Phe Leu Arg Leu Leu Ser Asn Ser Pro Leu Gln
    50                  55                  60

Val Asp Ile Gln Leu Leu Arg Ile Asp Ser Arg Glu Ser Arg Asn Thr
65                  70                  75                  80

Pro Ala Glu His Leu Asn Asn Phe Tyr Cys Asn Phe Glu Asp Ile Gln
                85                  90                  95

Asp Gln Asn Phe Asp Glu Thr Ile Val Thr Gly Ala Pro Leu Glu His
            100                 105                 110

Val Gly Phe Asn Asp Val Ala Tyr Trp Pro Gln Ile Lys Gln Val Leu
        115                 120                 125

Glu Trp Ser Lys Asp His Val Thr Ser Thr Leu Ser Val Cys Trp Ala
    130                 135                 140

Val Gln Ala Ala Leu Asn Ile Leu Tyr Gly Ile Pro Lys Gln Thr Arg
145                 150                 155                 160

Thr Glu Lys Leu Ser Gly Val Tyr Glu His His Ile Leu His Pro His
                165                 170                 175

Ala Leu Leu Thr Arg Gly Phe Asp Asp Ser Phe Leu Ala Pro His Ser
            180                 185                 190

Arg Tyr Ala Asp Phe Pro Ala Ala Leu Ile Arg Asp Tyr Thr Asp Leu
        195                 200                 205

Glu Ile Leu Ala Glu Thr Glu Glu Gly Asp Ala Tyr Leu Phe Ala Ser
    210                 215                 220

Lys Asp Lys Arg Ile Ala Phe Val Thr Gly His Pro Glu Tyr Asp Ala
225                 230                 235                 240

Gln Thr Leu Ala Gln Glu Phe Phe Arg Asp Val Glu Ala Gly Leu Asp
                245                 250                 255

Pro Asp Val Pro Tyr Asn Tyr Phe Pro His Asn Asp Pro Gln Asn Thr
            260                 265                 270

Pro Arg Ala Ser Trp Arg Ser His Gly Asn Leu Leu Phe Thr Asn Trp
        275                 280                 285

Leu Asn Tyr Tyr Val Tyr Gln Ile Thr Pro Tyr Asp Leu Arg His Met

Asn Pro Thr Leu Asp
305

<210> SEQ ID NO 24
<211> LENGTH: 930
<212> TYPE: DNA
<213> ORGANISM: Artificial Sequence
<220> FEATURE:
<223> OTHER INFORMATION: polynucleotide coding variant polypeptide metAEL

<400> SEQUENCE: 24

```
atgccgattc gtgtgccgga cgagctaccc gccgtcaatt tcttgcgtga agaaaacgtc      60
tttgtgatga caacttctcg tgcgtctggt caggaaattc gtccacttaa ggttctgatc     120
cttaacctga tgccgaagaa gattgaaact gaaaatcagt ttctgcgcct gctttcaaac     180
tcacctttgc aggtcgatat tcagctgttg cgcatcgatt cccgtgaatc gcgcaacacg     240
cccgcagagc atctgaacaa cttctactgt aactttgaag atattcagga tcagaacttt     300
gacggtttga ttgtaactgg tgcgccgctg gaactggtgg agtttaatga tgtcgcttac     360
tggccgcaga tcaaacaggt gctggagtgg tcgaaagatc acgtcacctc gacgctgttt     420
gtctgctggg cggtacaggc cgcgctcaat atcctctacg gcattcctaa gcaaactcgc     480
accgaaaaac tctctggcgt ttacgagcat catattctcc atcctcatgc gcttctgacg     540
cgtggctttg atgattcatt cctggcaccg cattcgcgct atgctgactt tccggcagcg     600
ttgattcgtg attacaccga tctggaaatt ctggcagaga cggaagaagg ggatgcatat     660
ctgtttgcca gtaaagataa gcgcattgcc tttgtgacgg ccatcccga atatgatgcg      720
caaacgctgg cgcaggaatt tttccgcgat gtggaagccg gactagaccc ggatgtaccg     780
tataactatt cccgcacaa tgatccgcaa aatacaccgc gagcgagctg cgtagtcac      840
ggtaatttac tgtttaccaa ctggctcaac tattacgtct accagatcac gccatacgat     900
ctacggcaca tgaatccaac gctggattaa                                      930
```

<210> SEQ ID NO 25
<211> LENGTH: 930
<212> TYPE: DNA
<213> ORGANISM: Artificial Sequence
<220> FEATURE:
<223> OTHER INFORMATION: polynucleotide coding variant polypeptide metAET

<400> SEQUENCE: 25

```
atgccgattc gtgtgccgga cgagctaccc gccgtcaatt tcttgcgtga agaaaacgtc      60
tttgtgatga caacttctcg tgcgtctggt caggaaattc gtccacttaa ggttctgatc     120
cttaacctga tgccgaagaa gattgaaact gaaaatcagt ttctgcgcct gctttcaaac     180
tcacctttgc aggtcgatat tcagctgttg cgcatcgatt cccgtgaatc gcgcaacacg     240
cccgcagagc atctgaacaa cttctactgt aactttgaag atattcagga tcagaacttt     300
gacggtttga ttgtaactgg tgcgccgctg gaaccgtgg agtttaatga tgtcgcttac      360
tggccgcaga tcaaacaggt gctggagtgg tcgaaagatc acgtcacctc gacgctgttt     420
gtctgctggg cggtacaggc cgcgctcaat atcctctacg gcattcctaa gcaaactcgc     480
accgaaaaac tctctggcgt ttacgagcat catattctcc atcctcatgc gcttctgacg     540
cgtggctttg atgattcatt cctggcaccg cattcgcgct atgctgactt tccggcagcg     600
```

```
ttgattcgtg attacaccga tctggaaatt ctggcagaga cggaagaagg ggatgcatat      660
ctgtttgcca gtaaagataa gcgcattgcc tttgtgacgg ccatcccga atatgatgcg       720 caaacgctgg cgcaggaatt tttccgcgat gtggaagccg actagaccc ggatgtaccg      780 tataactatt tcccgcacaa tgatccgcaa aatacaccgc gagcgagctg gcgtagtcac      840
ggtaatttac tgtttaccaa ctggctcaac tattacgtct accagatcac gccatacgat      900
ctacggcaca tgaatccaac gctggattaa                                       930

<210> SEQ ID NO 26
<211> LENGTH: 930
<212> TYPE: DNA
<213> ORGANISM: Artificial Sequence
<220> FEATURE:
<223> OTHER INFORMATION: polynucleotide coding variant polypeptide
      metAEH

<400> SEQUENCE: 26
atgccgattc gtgtgccgga cgagctaccc gccgtcaatt tcttgcgtga agaaaacgtc       60
tttgtgatga caacttctcg tgcgtctggt caggaaattc gtccacttaa ggttctgatc      120
cttaacctga tgccgaagaa gattgaaact gaaaatcagt ttctgcgcct gctttcaaac      180
tcacctttgc aggtcgatat tcagctgttg cgcatcgatt cccgtgaatc gcgcaacacg      240
cccgcagagc atctgaacaa cttctactgt aactttgaag atattcagga tcagaacttt      300
gacggtttga ttgtaactgg tgcgccgctg aacatgtgg agtttaatga tgtcgcttac       360
tggccgcaga tcaaacaggt gctggagtgg tcgaaagatc acgtcacctc gacgctgttt      420
gtctgctggg cggtacaggc cgcgctcaat atcctctacg gcattcctaa gcaaactcgc      480
accgaaaaac tctctggcgt ttacgagcat catattctcc atcctcatgc gcttctgacg      540
cgtggctttg atgattcatt cctggcaccg cattcgcgct atgctgactt tccggcagcg      600
ttgattcgtg attacaccga tctggaaatt ctggcagaga cggaagaagg ggatgcatat      660
ctgtttgcca gtaaagataa gcgcattgcc tttgtgacgg ccatcccga atatgatgcg       720 caaacgctgg cgcaggaatt tttccgcgat gtggaagccg actagaccc ggatgtaccg      780 tataactatt tcccgcacaa tgatccgcaa aatacaccgc gagcgagctg gcgtagtcac      840
ggtaatttac tgtttaccaa ctggctcaac tattacgtct accagatcac gccatacgat      900
ctacggcaca tgaatccaac gctggattaa                                       930

<210> SEQ ID NO 27
<211> LENGTH: 930
<212> TYPE: DNA
<213> ORGANISM: Artificial Sequence
<220> FEATURE:
<223> OTHER INFORMATION: polynucleotide coding variant polypeptide
      met11AEL

<400> SEQUENCE: 27
atgccgattc gtgtgccgga cgagctaccc gccgtcaatt tcttgcgtga agaaaacgtc       60
tttgtgatga caacttctcg tgcgcctggt caggaaattc gtccacttaa ggttctgatc      120
cttaacctga tgccgaagaa gattgaaact gaaaatcagt ttctgcgcct gctttcaaac      180
tcacctttgc aggtcgatat tcagctgttg cgcatcgatt cccgtgaatc gcgcaacacg      240
cccgcagagc atctgaacaa cttctactgt aactttgaag atattcagga tcagaacttt      300
gacggtttga ttgtaactgg tgcgccgctg aactggtgg ggtttaatga tgtcgcttac       360
tggccgcaga tcaaacaggt gctggagtgg tcgaaagatc acgtcacctc gacgctgtct      420
```

```
gtctgctggg cggtacaggc cgcgctcaat atcctctacg gcattcctaa gcaaactcgc    480
accgaaaaac tctctggcgt ttacgagcat catattctcc atcctcatgc gcttctgacg    540
cgtggctttg atgattcatt cctggcaccg cattcgcgct atgctgactt tccggcagcg    600
ttgattcgtg attacaccga tctggaaatt ctggcagaga cggaagaagg ggatgcatat    660
ctgtttgcca gtaaagataa gcgcattgcc tttgtgacgg ccatcccga atatgatgcg     720 caaacgctgg cgcaggaatt tttccgcgat gtggaagccg gactagaccc ggatgtaccg    780
tataactatt tcccgcacaa tgatccgcaa aatacaccgc gagcgagctg gcgtagtcac    840
ggtaatttac tgtttaccaa ctggctcaac tattacgtct accagatcac gccatacgat    900
ctacggcaca tgaatccaac gctggattaa                                     930

<210> SEQ ID NO 28
<211> LENGTH: 930
<212> TYPE: DNA
<213> ORGANISM: Artificial Sequence
<220> FEATURE:
<223> OTHER INFORMATION: polynucleotide coding variant polypeptide
      met11AET

<400> SEQUENCE: 28
atgccgattc gtgtgccgga cgagctaccc gccgtcaatt tcttgcgtga agaaaacgtc     60
tttgtgatga caacttctcg tgcgcctggt caggaaattc gtccacttaa ggttctgatc    120
cttaacctga tgccgaagaa gattgaaact gaaaatcagt ttctgcgcct gctttcaaac    180
tcacctttgc aggtcgatat tcagctgttg cgcatcgatt cccgtgaatc gcgcaacacg    240
cccgcagagc atctgaacaa cttctactgt aactttgaag atattcagga tcagaacttt    300
gacggtttga ttgtaactgg tgccgccgct gaaaccgtgg ggtttaatga tgtcgcttac    360
tggccgcaga tcaaacaggt gctggagtgg tcgaaagatc acgtcacctc gacgctgtct    420
gtctgctggg cggtacaggc cgcgctcaat atcctctacg gcattcctaa gcaaactcgc    480
accgaaaaac tctctggcgt ttacgagcat catattctcc atcctcatgc gcttctgacg    540
cgtggctttg atgattcatt cctggcaccg cattcgcgct atgctgactt tccggcagcg    600
ttgattcgtg attacaccga tctggaaatt ctggcagaga cggaagaagg ggatgcatat    660
ctgtttgcca gtaaagataa gcgcattgcc tttgtgacgg ccatcccga atatgatgcg     720 caaacgctgg cgcaggaatt tttccgcgat gtggaagccg gactagaccc ggatgtaccg    780
tataactatt tcccgcacaa tgatccgcaa aatacaccgc gagcgagctg gcgtagtcac    840
ggtaatttac tgtttaccaa ctggctcaac tattacgtct accagatcac gccatacgat    900
ctacggcaca tgaatccaac gctggattaa                                     930

<210> SEQ ID NO 29
<211> LENGTH: 930
<212> TYPE: DNA
<213> ORGANISM: Artificial Sequence
<220> FEATURE:
<223> OTHER INFORMATION: polynucleotide coding variant polypeptide
      met11AEH

<400> SEQUENCE: 29
atgccgattc gtgtgccgga cgagctaccc gccgtcaatt tcttgcgtga agaaaacgtc     60
tttgtgatga caacttctcg tgcgcctggt caggaaattc gtccacttaa ggttctgatc    120
cttaacctga tgccgaagaa gattgaaact gaaaatcagt ttctgcgcct gctttcaaac    180
```

```
tcacctttgc aggtcgatat tcagctgttg cgcatcgatt cccgtgaatc gcgcaacacg    240
cccgcagagc atctgaacaa cttctactgt aactttgaag atattcagga tcagaacttt    300
gacggtttga ttgtaactgg tgcgccgctg aacatgtggg gtttaatga tgtcgcttac    360 tggccgcaga tcaaacaggt gctggagtgg tcgaaagatc acgtcacctc gacgctgtct    420
gtctgctggg cggtacaggc cgcgctcaat atcctctacg gcattcctaa gcaaactcgc    480
accgaaaaac tctctggcgt ttacgagcat catattctcc atcctcatgc gcttctgacg    540
cgtggctttg atgattcatt cctggcaccg cattcgcgct atgctgactt ccggcagcg    600 ttgattcgtg attacaccga tctggaaatt ctggcagaga cggaagaagg ggatgcatat    660
ctgtttgcca gtaaagataa gcgcattgcc tttgtgacgg gccatcccga atatgatgcg    720
caaacgctgg cgcaggaatt tttccgcgat gtggaagccg gactagaccc ggatgtaccg    780
tataactatt tcccgcacaa tgatccgcaa aatacaccgc gagcgagctg gcgtagtcac    840
ggtaatttac tgtttaccaa ctggctcaac tattacgtct accagatcac gccatacgat    900
ctacggcaca tgaatccaac gctggattaa                                     930

<210> SEQ ID NO 30
<211> LENGTH: 134
<212> TYPE: DNA
<213> ORGANISM: Artificial Sequence
<220> FEATURE:
<223> OTHER INFORMATION: pro promoter nucletotide

<400> SEQUENCE: 30
tcgagcatag catttttatc cataagatta gcggatctaa cctttacaat tgtgagcgct     60
cacaattatg atagattcaa ttgtgagcgg ataacaattt cacacagaat tcattaaaga    120
ggagaaaggt acat                                                      134

<210> SEQ ID NO 31
<211> LENGTH: 61
<212> TYPE: DNA
<213> ORGANISM: Artificial Sequence
<220> FEATURE:
<223> OTHER INFORMATION: Primer

<400> SEQUENCE: 31
aggggcttca tccgaattgc gccattgttg caatggcggt gctggagctg cttcgaagtt     60
c                                                                     61

<210> SEQ ID NO 32
<211> LENGTH: 42
<212> TYPE: DNA
<213> ORGANISM: Artificial Sequence
<220> FEATURE:
<223> OTHER INFORMATION: Primer

<400> SEQUENCE: 32
gatattcata tggaccatgg ctcgagcata gcatttttat cc                        42

<210> SEQ ID NO 33
<211> LENGTH: 42
<212> TYPE: DNA
<213> ORGANISM: Artificial Sequence
<220> FEATURE:
<223> OTHER INFORMATION: Primer

<400> SEQUENCE: 33
ggataaaaat gctatgctcg agccatggtc catatgaata tc                        42
```

<210> SEQ ID NO 34
<211> LENGTH: 60
<212> TYPE: DNA
<213> ORGANISM: Artificial Sequence
<220> FEATURE:
<223> OTHER INFORMATION: Primer

<400> SEQUENCE: 34
cgatgttggc aggaatggtg tgtttgtgaa tttggctcat atgtaccttt ctcctctta      60

<210> SEQ ID NO 35
<211> LENGTH: 20
<212> TYPE: DNA
<213> ORGANISM: Artificial Sequence
<220> FEATURE:
<223> OTHER INFORMATION: Forward primer

<400> SEQUENCE: 35
atgagtataa aagagcaaac                                                 20

<210> SEQ ID NO 36
<211> LENGTH: 19
<212> TYPE: DNA
<213> ORGANISM: Artificial Sequence
<220> FEATURE:
<223> OTHER INFORMATION: Reverse primer

<400> SEQUENCE: 36
ttatttgcgt agtctgacc                                                  19

<210> SEQ ID NO 37
<211> LENGTH: 37
<212> TYPE: DNA
<213> ORGANISM: Artificial Sequence
<220> FEATURE:
<223> OTHER INFORMATION: Forward primer

<400> SEQUENCE: 37
ggaaaagtac aaccgccgcc gtattgcagg cgctatt                              37

<210> SEQ ID NO 38
<211> LENGTH: 37
<212> TYPE: DNA
<213> ORGANISM: Artificial Sequence
<220> FEATURE:
<223> OTHER INFORMATION: Reverse primer

<400> SEQUENCE: 38
aatagcgcct gcaatacggc ggcggttgta cttttcc                              37

<210> SEQ ID NO 39
<211> LENGTH: 930
<212> TYPE: DNA
<213> ORGANISM: Artificial Sequence
<220> FEATURE:
<223> OTHER INFORMATION: metA

<400> SEQUENCE: 39
atgccgattc gtgtgccgga cgagctaccc gccgtcaatt tcttgcgtga agaaaacgtc      60
tttgtgatga caacttctcg tgcgtctggt caggaaattc gtccacttaa ggttctgatc     120
cttaacctga tgccgaagaa gattgaaact gaaaatcagt ttctgcgcct gctttcaaac     180
tcacctttgc aggtcgatat tcagctgttg cgcatcgatt cccgtgaatc gcgcaacacg     240

```
cccgcagagc atctgaacaa cttctactgt aactttgaag atattcagga tcagaacttt    300
gacggtttga ttgtaactgg tgcgccgctg ggcctggtgg agtttaatga tgtcgcttac    360
tggccgcaga tcaaacaggt gctggagtgg tcgaaagatc acgtcacctc gacgctgttt    420
gtctgctggg cggtacaggc cgcgctcaat atcctctacg gcattcctaa gcaaactcgc    480
accgaaaaac tctctggcgt ttacgagcat catattctcc atcctcatgc gcttctgacg    540
cgtggctttg atgattcatt cctggcaccg cattcgcgct atgctgactt ccgcagcg     600 ttgattcgtg attacaccga tctggaaatt ctggcagaga cggaagaagg ggatgcatat    660
ctgtttgcca gtaaagataa gcgcattgcc tttgtgacgg ccatcccga atatgatgcg     720 caaacgctgg cgcaggaatt tttccgcgat gtggaagccg actagaccc ggatgtaccg     780 tataactatt tcccgcacaa tgatccgcaa aatacaccgc gagcgagctg gcgtagtcac    840
ggtaatttac tgtttaccaa ctggctcaac tattacgtct accagatcac gccatacgat    900
ctacggcaca tgaatccaac gctggattaa                                     930
```

```
<210> SEQ ID NO 40
<211> LENGTH: 316
<212> TYPE: PRT
<213> ORGANISM: Artificial Sequence
<220> FEATURE:
<223> OTHER INFORMATION: feedback resistant coaA coaA R106A

<400> SEQUENCE: 40

Met Ser Ile Lys Glu Gln Thr Leu Met Thr Pro Tyr Leu Gln Phe Asp
1               5                   10                  15

Arg Asn Gln Trp Ala Ala Leu Arg Asp Ser Val Pro Met Thr Leu Ser
            20                  25                  30

Glu Asp Glu Ile Ala Arg Leu Lys Gly Ile Asn Glu Asp Leu Ser Leu
        35                  40                  45

Glu Glu Val Ala Glu Ile Tyr Leu Pro Leu Ser Arg Leu Leu Asn Phe
    50                  55                  60

Tyr Ile Ser Ser Asn Leu Arg Arg Gln Ala Val Leu Glu Gln Phe Leu
65                  70                  75                  80

Gly Thr Asn Gly Gln Arg Ile Pro Tyr Ile Ile Ser Ile Ala Gly Ser
                85                  90                  95

Val Ala Val Gly Lys Ser Thr Thr Ala Arg Val Leu Gln Ala Leu Leu
            100                 105                 110

Ser Arg Trp Pro Glu His Arg Arg Val Glu Leu Ile Thr Thr Asp Gly
        115                 120                 125

Phe Leu His Pro Asn Gln Val Leu Lys Glu Arg Gly Leu Met Lys Lys
    130                 135                 140

Lys Gly Phe Pro Glu Ser Tyr Asp Met His Arg Leu Val Lys Phe Val
145                 150                 155                 160

Ser Asp Leu Lys Ser Gly Val Pro Asn Val Thr Ala Pro Val Tyr Ser
                165                 170                 175

His Leu Ile Tyr Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
        195                 200                 205

Asp Tyr Pro His Asp Pro His His Val Phe Val Ser Asp Phe Val Asp
    210                 215                 220

Phe Ser Ile Tyr Val Asp Ala Pro Glu Asp Leu Leu Gln Thr Trp Tyr
225                 230                 235                 240
```

```
Ile Asn Arg Phe Leu Lys Phe Arg Glu Gly Ala Phe Thr Asp Pro Asp
                245                 250                 255

Ser Tyr Phe His Asn Tyr Ala Lys Leu Thr Lys Glu Glu Ala Ile Lys
            260                 265                 270

Thr Ala Met Thr Leu Trp Lys Glu Ile Asn Trp Leu Asn Leu Lys Gln
        275                 280                 285

Asn Ile Leu Pro Thr Arg Glu Arg Ala Ser Leu Ile Leu Thr Lys Ser
    290                 295                 300

Ala Asn His Ala Val Glu Glu Val Arg Leu Arg Lys
305                 310                 315

<210> SEQ ID NO 41
<211> LENGTH: 309
<212> TYPE: PRT
<213> ORGANISM: Artificial Sequence
<220> FEATURE:
<223> OTHER INFORMATION: ECOHS E. coli O9 H4 strain HS

<400> SEQUENCE: 41

Met Pro Ile Arg Val Pro Asp Glu Leu Pro Ala Val Asn Phe Leu Arg
 1               5                  10                  15

Glu Glu Asn Val Phe Val Met Thr Thr Ser Arg Ala Ser Gly Gln Glu
            20                  25                  30

Ile Arg Pro Leu Lys Val Leu Ile Leu Asn Leu Met Pro Lys Lys Ile
        35                  40                  45

Glu Thr Glu Asn Gln Phe Leu Arg Leu Leu Ser Asn Ser Pro Leu Gln
    50                  55                  60

Val Asp Ile Gln Leu Leu Arg Ile Asp Ser Arg Glu Ser Arg Asn Thr
65                  70                  75                  80

Pro Ala Glu His Leu Asn Asn Phe Tyr Cys Asn Phe Glu Asp Ile Gln
                85                  90                  95

Glu Gln Asn Phe Asp Gly Leu Ile Val Thr Gly Ala Pro Leu Gly Leu
            100                 105                 110

Val Glu Phe Asn Asp Val Ala Tyr Trp Pro Gln Ile Lys Gln Val Leu
        115                 120                 125

Glu Trp Ser Lys Asp His Val Thr Ser Thr Leu Phe Val Cys Trp Ala
    130                 135                 140

Val Gln Ala Ala Leu Asn Ile Leu Tyr Gly Ile Pro Lys Gln Thr Arg
145                 150                 155                 160

Thr Asp Lys Leu Ser Gly Val Tyr Glu His His Ile Leu His Pro His
                165                 170                 175

Ala Leu Leu Thr Arg Gly Phe Asp Asp Ser Phe Leu Ala Pro His Ser
            180                 185                 190

Arg Tyr Ala Asp Phe Pro Ala Ala Leu Ile Arg Asp Tyr Thr Asp Leu
        195                 200                 205

Glu Ile Leu Ala Glu Thr Glu Glu Gly Asp Ala Tyr Leu Phe Ala Ser
    210                 215                 220

Lys Asp Lys Arg Ile Ala Phe Val Thr Gly His Pro Glu Tyr Asp Ala
225                 230                 235                 240

Gln Thr Leu Ala Gln Glu Tyr Phe Arg Asp Val Glu Ala Gly Leu Gly
                245                 250                 255

Pro Glu Val Pro Tyr Asn Tyr Phe Pro His Asn Asp Pro Gln Asn Thr
            260                 265                 270

Pro Arg Ala Ser Trp Arg Ser His Gly Asn Leu Leu Phe Thr Asn Trp
        275                 280                 285
```

Leu Asn Tyr Tyr Val Tyr Gln Ile Thr Pro Tyr Asp Leu Arg His Met
        290                 295                 300

Asn Pro Thr Leu Asp
305

<210> SEQ ID NO 42
<211> LENGTH: 309
<212> TYPE: PRT
<213> ORGANISM: Artificial Sequence
<220> FEATURE:
<223> OTHER INFORMATION: ECO24 E. coli O139 H28 strain E24377A

<400> SEQUENCE: 42

Met Pro Ile Arg Val Pro Asp Glu Leu Pro Ala Val Asn Phe Leu Arg
 1               5                  10                  15

Glu Glu Asn Val Phe Val Met Thr Thr Ser Arg Ala Ser Gly Gln Glu
            20                  25                  30

Ile Arg Pro Leu Lys Val Leu Ile Leu Asn Leu Met Pro Lys Lys Ile
        35                  40                  45

Glu Thr Glu Asn Gln Phe Leu Arg Leu Leu Ser Asn Ser Pro Leu Gln
    50                  55                  60

Val Asp Ile Gln Leu Leu Arg Ile Asp Ser Arg Glu Ser Arg Asn Thr
65                  70                  75                  80

Pro Ala Glu His Leu Asn Asn Phe Tyr Cys Asn Phe Glu Asp Ile Gln
                85                  90                  95

Glu Gln Asn Phe Asp Gly Leu Ile Val Thr Gly Ala Pro Leu Gly Leu
            100                 105                 110

Val Glu Phe Asn Asp Val Ala Tyr Trp Pro Gln Ile Lys Gln Val Leu
        115                 120                 125

Glu Trp Ser Lys Asp His Val Thr Ser Thr Leu Phe Val Cys Trp Ala
130                 135                 140

Val Gln Ala Ala Leu Asn Ile Leu Tyr Gly Ile Pro Lys Gln Thr Arg
145                 150                 155                 160

Thr Asp Lys Leu Ser Gly Val Tyr Glu His His Ile Leu His Pro His
                165                 170                 175

Ala Leu Leu Thr Arg Gly Phe Asp Asp Ser Phe Leu Ala Pro His Ser
            180                 185                 190

Arg Tyr Ala Asp Phe Pro Ala Ala Leu Ile Arg Asp Tyr Thr Asp Leu
        195                 200                 205

Glu Ile Leu Ala Glu Thr Glu Glu Gly Asp Ala Tyr Leu Phe Ala Ser
    210                 215                 220

Lys Asp Lys Arg Ile Ala Phe Val Thr Gly His Pro Glu Tyr Asp Ala
225                 230                 235                 240

Gln Thr Leu Ala Gln Glu Tyr Phe Arg Asp Val Glu Ala Gly Leu Gly
                245                 250                 255

Pro Glu Val Pro Tyr Asn Tyr Phe Pro His Asn Asp Pro Gln Asn Thr
            260                 265                 270

Pro Arg Ala Ser Trp Arg Ser His Gly Asn Leu Leu Phe Thr Asn Trp
        275                 280                 285

Leu Asn Tyr Tyr Val Tyr Gln Ile Thr Pro Tyr Asp Leu Arg His Met
    290                 295                 300

Asn Pro Thr Leu Asp
305

<210> SEQ ID NO 43
<211> LENGTH: 309

```
<212> TYPE: PRT
<213> ORGANISM: Artificial Sequence
<220> FEATURE:
<223> OTHER INFORMATION: ECO57 E. coli O157 H7 E. coli strain ATCC8739

<400> SEQUENCE: 43
```

| | | | | | | | | | | | | | | | |
|---|---|---|---|---|---|---|---|---|---|---|---|---|---|---|---|
| Met | Pro | Ile | Arg | Val | Pro | Asp | Glu | Leu | Pro | Ala | Val | Asn | Phe | Leu | Arg |
| 1 | | | | 5 | | | | | 10 | | | | | 15 | |
| Glu | Glu | Asn | Val | Phe | Val | Met | Thr | Thr | Ser | Arg | Ala | Ser | Gly | Gln | Glu |
| | | | 20 | | | | | 25 | | | | | 30 | | |
| Ile | Arg | Pro | Leu | Lys | Val | Leu | Ile | Leu | Asn | Leu | Met | Pro | Lys | Lys | Ile |
| | | | 35 | | | | | 40 | | | | | 45 | | |
| Glu | Thr | Glu | Asn | Gln | Phe | Leu | Arg | Leu | Leu | Ser | Asn | Ser | Pro | Leu | Gln |
| | 50 | | | | | 55 | | | | | 60 | | | | |
| Val | Asp | Ile | Gln | Leu | Leu | Arg | Ile | Asp | Ser | Arg | Glu | Ser | Arg | Asn | Thr |
| 65 | | | | | 70 | | | | | 75 | | | | | 80 |
| Pro | Ala | Glu | His | Leu | Asn | Asn | Phe | Tyr | Cys | Asn | Phe | Glu | Asp | Ile | Gln |
| | | | | 85 | | | | | 90 | | | | | 95 | |
| Glu | Gln | Asn | Phe | Asp | Gly | Leu | Ile | Val | Thr | Gly | Ala | Pro | Leu | Gly | Leu |
| | | | 100 | | | | | 105 | | | | | 110 | | |
| Val | Glu | Phe | Asn | Asp | Val | Ala | Tyr | Trp | Pro | Gln | Ile | Lys | Gln | Val | Leu |
| | | | 115 | | | | | 120 | | | | | 125 | | |
| Glu | Trp | Ser | Lys | Asp | His | Val | Thr | Ser | Thr | Leu | Phe | Val | Cys | Trp | Ala |
| | 130 | | | | | 135 | | | | | 140 | | | | |
| Val | Gln | Ala | Ala | Leu | Asn | Ile | Leu | Tyr | Gly | Ile | Pro | Lys | Gln | Thr | Arg |
| 145 | | | | | 150 | | | | | 155 | | | | | 160 |
| Thr | Asp | Lys | Leu | Ser | Gly | Val | Tyr | Glu | His | His | Ile | Leu | His | Pro | His |
| | | | | 165 | | | | | 170 | | | | | 175 | |
| Ala | Leu | Leu | Thr | Arg | Gly | Phe | Asp | Asp | Ser | Phe | Leu | Ala | Pro | His | Ser |
| | | | 180 | | | | | 185 | | | | | 190 | | |
| Arg | Tyr | Ala | Asp | Phe | Pro | Ala | Ala | Leu | Ile | Arg | Asp | Tyr | Thr | Asp | Leu |
| | | | 195 | | | | | 200 | | | | | 205 | | |
| Glu | Ile | Leu | Ala | Glu | Thr | Glu | Glu | Gly | Asp | Ala | Tyr | Leu | Phe | Ala | Ser |
| | 210 | | | | | 215 | | | | | 220 | | | | |
| Lys | Asp | Lys | Arg | Ile | Ala | Phe | Val | Thr | Gly | His | Pro | Glu | Tyr | Asp | Ala |
| 225 | | | | | 230 | | | | | 235 | | | | | 240 |
| Gln | Thr | Leu | Ala | Gln | Glu | Tyr | Phe | Arg | Asp | Val | Glu | Ala | Gly | Leu | Asp |
| | | | | 245 | | | | | 250 | | | | | 255 | |
| Pro | Glu | Val | Pro | Tyr | Asn | Tyr | Phe | Pro | His | Asn | Asp | Pro | Gln | Asn | Lys |
| | | | 260 | | | | | 265 | | | | | 270 | | |
| Pro | Arg | Ala | Ser | Trp | Arg | Ser | His | Gly | Asn | Leu | Leu | Phe | Thr | Asn | Trp |
| | | | 275 | | | | | 280 | | | | | 285 | | |
| Leu | Asn | Tyr | Tyr | Val | Tyr | Gln | Ile | Thr | Pro | Tyr | Asp | Leu | Arg | His | Met |
| | 290 | | | | | 295 | | | | | 300 | | | | |
| Asn | Pro | Thr | Leu | Asp | | | | | | | | | | | |
| 305 | | | | | | | | | | | | | | | |

```
<210> SEQ ID NO 44
<211> LENGTH: 2464
<212> TYPE: DNA
<213> ORGANISM: Artificial Sequence
<220> FEATURE:
<223> OTHER INFORMATION: metX Deinococcus radiodurans

<400> SEQUENCE: 44
atgcgagtgt tgaagttcgg cggtacatca gtggcaaatg cagaacgttt tctgcgtgtt      60
```

-continued

```
gccgatattc tggaaagcaa tgccaggcag gggcaggtgg ccaccgtcct ctctgccccc      120
gccaaaatca ccaaccacct ggtggcgatg attgaaaaaa ccattagcgg ccaggatgct      180
ttacccaata tcagcgatgc cgaacgtatt tttgccgaac ttttgacggg actcgccgcc      240
gcccagccgg ggttcccgct ggcgcaattg aaaactttcg tcgatcagga atttgcccaa      300
ataaaacatg tcctgcatgg cattagtttg ttggggcagt gcccggatag catcaacgct      360
gcgctgattt gccgtggcga gaaaatgtcg atcgccatta tggccggcgt attagaagcg      420
cgcggtcaca acgttactgt tatcgatccg gtcgaaaaac tgctggcagt ggggcattac      480
ctcgaatcta ccgtcgatat tgctgagtcc acccgccgta ttgcggcaag ccgcattccg      540
gctgatcaca tggtgctgat ggcaggtttc accgccggta atgaaaaagg cgaactggtg      600
gtgcttggac gcaacggttc cgactactct gctgcggtgc tggctgcctg tttacgcgcc      660
gattgttgcg agatttggac ggacgttgac ggggtctata cctgcgaccc gcgtcaggtg      720
cccgatgcga ggttgttgaa gtcgatgtcc taccaggaag cgatggagct ttcctacttc      780
ggcgctaaag ttcttcaccc ccgcaccatt accccccatcg cccagttcca gatcccttgc      840
ctgattaaaa ataccggaaa tcctcaagca ccaggtacgc tcattggtgc cagccgtgat      900
gaagacgaat taccggtcaa gggcatttcc aatctgaata acatggcaat gttcagcgtt      960
tctggtccgg ggatgaaagg gatggtcggc atggcggcgc gcgtctttgc agcgatgtca     1020
cgcgcccgta ttttcgtggt gctgattacg caatcatctt ccgaatacag catcagtttc     1080
tgcgttccac aaagcgactg tgtgcgagct gaacgggcaa tgcaggaaga gttctacctg     1140
gaactgaaag aaggcttact ggagccgctg gcagtgacgg aacggctggc cattatctcg     1200
gtggtaggtg atggtatgcg caccttgcgt gggatctcgg cgaaattctt tgccgcactg     1260
gcccgcgcca atatcaacat tgtcgccatt gctcagggat cttctgaacg ctcaatctct     1320
gtcgtggtaa ataacgatga tgcgaccact ggcgtgcgcg ttactcatca gatgctgttc     1380
aataccgatc aggttatcga agtgtttgtg attggcgtcg gtggcgttgg cggtgcgctg     1440
ctggagcaac tgaagcgtca gcaaagctgg ctgaagaata acatatcga cttacgtgtc     1500 tgcggtgttg ccaactcgaa ggctctgctc accaatgtac atggccttaa tctggaaaac     1560
tggcaggaag aactggcgca agccaaagag ccgtttaatc tcgggcgctt aattcgcctc     1620
gtgaaagaat atcatctgct gaacccggtc attgttgact gcacttccag ccaggcagtg     1680
gcggatcaat atgccgactt cctgcgcgaa ggtttccacg ttgtcacgcc gaacaaaaag     1740
gccaacacct cgtcgatgga ttactaccat cagttgcgtt atgcggcgga aaaatcgcgg     1800
cgtaaattcc tctatgacac caacgttggg gctggattac cggttattga gaacctgcaa     1860
aatctgctca atgcaggtga tgaattgatg aagttctccg gcattctttc tggttcgctt     1920
tcttatatct tcggcaagtt agacgaaggc atgagtttct ccgaggcgac cacgctggcg     1980
cgggaaatgg ttataccgga accggacccg cgagatgatc tttctggtat ggatgtggcg     2040
cgtaaactat tgattctcgc tcgtgaaacg ggacgtgaac tggagctggc ggatattgaa     2100
attgaacctg tgctgcccgc agagtttaac gccgagggtg atgttgccgc ttttatggcg     2160
aatctgtcac aactcgacga tctctttgcc gcgcgcgtgg cgaaggcccg tgatgaagga     2220
aaagttttgc gctatgttgg caatattgat gaagatggcg tctgccgcgt gaagattgcc     2280
gaagtggatg gtaatgatcc gctgttcaaa gtgaaaaatg gcgaaaacgc cctggccttc     2340
tatagccact attatcagcc gctgccgttg gtactgcgcg gatatggtgc gggcaatgac     2400
gttacagctg ccggtgtctt tgctgatctg ctacgtaccc tctcatggaa gttaggagtc     2460
``` tgaa                                                                2464

<210> SEQ ID NO 45
<211> LENGTH: 309
<212> TYPE: PRT
<213> ORGANISM: Artificial Sequence
<220> FEATURE:
<223> OTHER INFORMATION: ECOLC E.coli META_ECOLC

<400> SEQUENCE: 45

Met Pro Ile Arg Val Pro Asp Glu Leu Pro Ala Val Asn Phe Leu Arg
 1               5                  10                  15

Glu Glu Asn Val Phe Val Met Thr Thr Ser Arg Ala Ser Gly Gln Glu
            20                  25                  30

Ile Arg Pro Leu Lys Val Leu Ile Leu Asn Leu Met Pro Lys Lys Ile
        35                  40                  45

Glu Thr Glu Asn Gln Phe Leu Arg Leu Leu Ser Asn Ser Pro Leu Gln
    50                  55                  60

Val Asp Ile Gln Leu Leu Arg Ile Asp Ser Arg Glu Ser Arg Asn Thr
65                  70                  75                  80

Pro Ala Glu His Leu Asn Asn Phe Tyr Cys Asn Phe Glu Asp Ile Gln
                85                  90                  95

Glu Gln Asn Phe Asp Gly Leu Ile Val Thr Gly Ala Pro Leu Gly Leu
            100                 105                 110

Val Glu Phe Asn Asp Val Ala Tyr Trp Pro Gln Ile Lys Gln Val Leu
        115                 120                 125

Glu Trp Ser Lys Asp His Val Thr Ser Thr Leu Phe Val Cys Trp Ala
    130                 135                 140

Val Gln Ala Ala Leu Asn Ile Leu Tyr Gly Ile Pro Lys Gln Thr Arg
145                 150                 155                 160

Thr Asp Lys Leu Ser Gly Val Tyr Glu His His Ile Leu His Pro His
                165                 170                 175

Ala Leu Leu Thr Arg Gly Phe Asp Asp Ser Phe Leu Ala Pro His Ser
            180                 185                 190

Arg Tyr Ala Asp Phe Pro Ala Ala Leu Ile Arg Asp Tyr Thr Asp Leu
        195                 200                 205

Glu Ile Leu Ala Glu Thr Glu Glu Gly Asp Ala Tyr Leu Phe Ala Ser
    210                 215                 220

Lys Asp Lys Arg Ile Ala Phe Val Thr Gly His Pro Glu Tyr Asp Ala
225                 230                 235                 240

Gln Thr Leu Ala Gln Glu Phe Phe Arg Asp Val Glu Ala Gly Leu Asp
                245                 250                 255

Pro Glu Val Pro Tyr Asn Tyr Phe Pro His Asn Asp Pro Gln Asn Thr
            260                 265                 270

Pro Arg Ala Ser Trp Arg Ser His Gly Asn Leu Leu Phe Thr Asn Trp
        275                 280                 285

Leu Asn Tyr Tyr Val Tyr Gln Ile Thr Pro Tyr Asp Leu Arg His Met
    290                 295                 300

Asn Pro Thr Leu Asp
305

<210> SEQ ID NO 46
<211> LENGTH: 309
<212> TYPE: PRT
<213> ORGANISM: Artificial Sequence
<220> FEATURE:

<223> OTHER INFORMATION: FBR met10A CJ feedback-resistance variant
    polypeptide having homoserine
    O-succinyltransferase activity

<400> SEQUENCE: 46

Met Pro Ile Arg Val Pro Asp Glu Leu Pro Ala Val Asn Phe Leu Arg
1               5                   10                  15

Glu Glu Asn Val Phe Val Met Thr Thr Ser Arg Ala Ser Gly Gln Glu
            20                  25                  30

Ile Arg Pro Leu Lys Val Leu Ile Leu Asn Leu Met Pro Lys Lys Ile
        35                  40                  45

Glu Thr Glu Asn Gln Phe Leu Arg Leu Ser Asn Ser Pro Leu Gln
    50                  55                  60

Val Asp Ile Gln Leu Leu Arg Ile Asp Ser Arg Glu Ser Arg Asn Thr
65                  70                  75                  80

Pro Ala Glu His Leu Asn Asn Phe Tyr Cys Asn Phe Glu Asp Ile Gln
                85                  90                  95

Asp Gln Asn Phe Asp Gly Leu Ile Val Thr Gly Ala Pro Leu Gly Leu
            100                 105                 110

Val Glu Phe Asn Asp Val Ala Tyr Trp Pro Gln Ile Lys Gln Val Leu
        115                 120                 125

Glu Trp Ser Lys Asp His Val Thr Ser Thr Leu Phe Val Cys Trp Ala
    130                 135                 140

Val Gln Ala Ala Leu Asn Ile Leu Tyr Gly Ile Pro Lys Gln Thr Arg
145                 150                 155                 160

Thr Glu Lys Leu Ser Gly Val Tyr Glu His His Ile Leu His Pro His
                165                 170                 175

Ala Leu Leu Thr Arg Gly Phe Asp Asp Ser Phe Leu Ala Pro His Ser
            180                 185                 190

Arg Tyr Ala Asp Phe Pro Ala Ala Leu Ile Arg Asp Tyr Thr Asp Leu
        195                 200                 205

Glu Ile Leu Ala Glu Thr Glu Glu Gly Asp Ala Tyr Leu Phe Ala Ser
    210                 215                 220

Lys Asp Lys Arg Ile Ala Phe Val Thr Gly His Pro Glu Tyr Asp Ala
225                 230                 235                 240

Gln Thr Leu Ala Gln Glu Phe Phe Arg Asp Val Glu Ala Gly Leu Asp
                245                 250                 255

Pro Asp Val Pro Tyr Asn Tyr Phe Pro His Asn Asp Pro Gln Asn Thr
            260                 265                 270

Pro Arg Ala Ser Trp Arg Ser His Gly Asn Leu Leu Phe Thr Asn Trp
        275                 280                 285

Leu His Tyr Tyr Val Tyr Gln Ile Thr Pro Tyr Asp Leu Arg His Met
    290                 295                 300

Asn Pro Thr Leu Asp
305

<210> SEQ ID NO 47
<211> LENGTH: 309
<212> TYPE: PRT
<213> ORGANISM: Artificial Sequence
<220> FEATURE:
<223> OTHER INFORMATION: FBR met11A CJ feedback-resistance variant
    polypeptide having homoserine
    O-succinyltransferase activity

<400> SEQUENCE: 47

Met Pro Ile Arg Val Pro Asp Glu Leu Pro Ala Val Asn Phe Leu Arg

```
            1               5                   10                  15
          Glu Glu Asn Val Phe Val Met Thr Thr Ser Arg Ala Pro Gly Gln Glu
                          20                  25                  30

Ile Arg Pro Leu Lys Val Leu Ile Leu Asn Leu Met Pro Lys Lys Ile
                          35                  40                  45

Glu Thr Glu Asn Gln Phe Leu Arg Leu Leu Ser Asn Ser Pro Leu Gln
                          50                  55                  60

Val Asp Ile Gln Leu Leu Arg Ile Asp Ser Arg Glu Ser Arg Asn Thr
          65                  70                  75                  80

Pro Ala Glu His Leu Asn Asn Phe Tyr Cys Asn Phe Glu Asp Ile Gln
                          85                  90                  95

Asp Gln Asn Phe Asp Gly Leu Ile Val Thr Gly Ala Pro Leu Gly Leu
                          100                 105                 110

Val Gly Phe Asn Asp Val Ala Tyr Trp Pro Gln Ile Lys Gln Val Leu
                          115                 120                 125

Glu Trp Ser Lys Asp His Val Thr Ser Thr Leu Pro Val Cys Trp Ala
          130                 135                 140

Val Gln Ala Ala Leu Asn Ile Leu Tyr Gly Ile Pro Lys Gln Thr Arg
          145                 150                 155                 160

Thr Glu Lys Leu Ser Gly Val Tyr Glu His Ile Leu His Pro His
                          165                 170                 175

Ala Leu Leu Thr Arg Gly Phe Asp Asp Ser Phe Leu Ala Pro His Ser
                          180                 185                 190

Arg Tyr Ala Asp Phe Pro Ala Ala Leu Ile Arg Asp Tyr Thr Asp Leu
                          195                 200                 205

Glu Ile Leu Ala Glu Thr Glu Glu Gly Asp Ala Tyr Leu Phe Ala Ser
                          210                 215                 220

Lys Asp Lys Arg Ile Ala Phe Val Thr Gly His Pro Glu Tyr Asp Ala
          225                 230                 235                 240

Gln Thr Leu Ala Gln Glu Phe Phe Arg Asp Val Glu Ala Gly Leu Asp
                          245                 250                 255

Pro Asp Val Pro Tyr Asn Tyr Phe Pro His Asn Asp Pro Gln Asn Thr
                          260                 265                 270

Pro Arg Ala Ser Trp Arg Ser His Gly Asn Leu Leu Phe Thr Asn Trp
                          275                 280                 285

Leu Asn Tyr Tyr Val Tyr Gln Ile Thr Pro Tyr Asp Leu Arg His Met
                          290                 295                 300

Asn Pro Thr Leu Asp
          305

<210> SEQ ID NO 48
          <211> LENGTH: 309
          <212> TYPE: PRT
          <213> ORGANISM: Artificial Sequence
          <220> FEATURE:
          <223> OTHER INFORMATION: FBR metA ME feedback-resistance variant
               polypeptide having homoserine
               O-succinyltransferase activity

<400> SEQUENCE: 48

Met Pro Ile Arg Val Pro Asp Glu Leu Pro Ala Val Asn Phe Leu Arg
          1               5                   10                  15

Glu Glu Asn Val Phe Val Met Thr Thr Ser Arg Val Ser Gly Gln Glu
                          20                  25                  30

Ile Arg Pro Leu Lys Val Leu Ile Leu Asn Leu Met Pro Lys Lys Ile
                          35                  40                  45
```

```
Glu Thr Glu Asn Gln Phe Leu Arg Leu Leu Ser Asn Ser Pro Phe Glu
     50                  55                  60

Val Asp Ile Gln Leu Leu Arg Ile Asp Ser Arg Glu Ser Arg Asn Thr
 65                  70                  75                  80

Pro Ala Glu His Leu Asn Asn Phe Tyr Cys Asn Phe Glu Asp Ile Gln
                 85                  90                  95

Asp Gln Asn Phe Asp Gly Leu Ile Val Thr Gly Ala Pro Leu Gly Leu
            100                 105                 110

Val Glu Phe Asn Asp Val Ala Tyr Trp Pro Gln Ile Lys Gln Val Leu
            115                 120                 125

Glu Trp Ser Lys Asp His Val Thr Ser Thr Leu Phe Val Cys Trp Ala
            130                 135                 140

Val Gln Ala Ala Leu Asn Ile Leu Tyr Gly Ile Pro Lys Gln Thr Arg
145                 150                 155                 160

Thr Glu Lys Leu Ser Gly Val Tyr Glu His His Ile Leu His Pro His
                165                 170                 175

Ala Leu Leu Thr Arg Gly Phe Asp Asp Ser Phe Leu Ala Pro His Ser
            180                 185                 190

Arg Tyr Ala Asp Phe Pro Ala Ala Leu Ile Arg Asp Tyr Thr Asp Leu
            195                 200                 205

Glu Ile Leu Ala Glu Thr Glu Glu Gly Asp Ala Tyr Leu Phe Ala Ser
210                 215                 220

Lys Asp Lys Arg Ile Ala Phe Val Thr Gly His Pro Glu Tyr Asp Ala
225                 230                 235                 240

Gln Thr Leu Ala Gln Glu Phe Phe Arg Asp Val Glu Ala Gly Leu Asp
            245                 250                 255

Pro Asp Val Pro Tyr Asn Tyr Phe Pro His Asn Asp Pro Gln Asn Thr
            260                 265                 270

Pro Arg Ala Ser Trp Arg Ser His Gly Asn Leu Leu Phe Thr Asn Trp
            275                 280                 285

Leu Asn Tyr Tyr Val Tyr Gln Ile Thr Pro Tyr Asp Leu Arg His Met
            290                 295                 300

Asn Pro Thr Leu Asp
305

<210> SEQ ID NO 49
<211> LENGTH: 309
<212> TYPE: PRT
<213> ORGANISM: Artificial Sequence
<220> FEATURE:
<223> OTHER INFORMATION: Consensus sequence
<220> FEATURE:
<221> NAME/KEY: VARIANT
<222> LOCATION: 256
<223> OTHER INFORMATION: Xaa = Asp or Gly

<400> SEQUENCE: 49

Met Pro Ile Arg Val Pro Asp Glu Leu Pro Ala Val Asn Phe Leu Arg
  1               5                  10                  15

Glu Glu Asn Val Phe Val Met Thr Thr Ser Arg Ala Ser Gly Gln Glu
             20                  25                  30

Ile Arg Pro Leu Lys Val Leu Leu Asn Leu Met Pro Lys Lys Ile
         35                  40                  45

Glu Thr Glu Asn Gln Phe Leu Arg Leu Ser Asn Ser Pro Leu Gln
     50                  55                  60

Val Asp Ile Gln Leu Leu Arg Ile Asp Ser Arg Glu Ser Arg Asn Thr
```

```
            65                  70                  75                  80
    Pro Ala Glu His Leu Asn Asn Phe Tyr Cys Asn Phe Glu Asp Ile Gln
                        85                  90                  95
    Glu Gln Asn Phe Asp Gly Leu Ile Val Thr Gly Ala Pro Leu Gly Leu
                    100                 105                 110
    Val Glu Phe Asn Asp Val Ala Tyr Trp Pro Gln Ile Lys Gln Val Leu
                115                 120                 125
    Glu Trp Ser Lys Asp His Val Thr Ser Thr Leu Phe Val Cys Trp Ala
    130                 135                 140
    Val Gln Ala Ala Leu Asn Ile Leu Tyr Gly Ile Pro Lys Gln Thr Arg
    145                 150                 155                 160
    Thr Asp Lys Leu Ser Gly Val Tyr Glu His His Ile Leu His Pro His
                    165                 170                 175
    Ala Leu Leu Thr Arg Gly Phe Asp Asp Ser Phe Leu Ala Pro His Ser
                180                 185                 190
    Arg Tyr Ala Asp Phe Pro Ala Ala Leu Ile Arg Asp Tyr Thr Asp Leu
                195                 200                 205
    Glu Ile Leu Ala Glu Thr Glu Glu Gly Asp Ala Tyr Leu Phe Ala Ser
            210                 215                 220
    Lys Asp Lys Arg Ile Ala Phe Val Thr Gly His Pro Glu Tyr Asp Ala
    225                 230                 235                 240
    Gln Thr Leu Ala Gln Glu Tyr Phe Arg Asp Val Glu Ala Gly Leu Xaa
                    245                 250                 255
    Pro Glu Val Pro Tyr Asn Tyr Phe Pro His Asn Asp Pro Gln Asn Thr
                260                 265                 270
    Pro Arg Ala Ser Trp Arg Ser His Gly Asn Leu Leu Phe Thr Asn Trp
                275                 280                 285
    Leu Asn Tyr Tyr Val Tyr Gln Ile Thr Pro Tyr Asp Leu Arg His Met
                290                 295                 300
    Asn Pro Thr Leu Asp
    305

<210> SEQ ID NO 50
<211> LENGTH: 309
<212> TYPE: PRT
<213> ORGANISM: Artificial Sequence
<220> FEATURE:
<223> OTHER INFORMATION: Sequence logo
<220> FEATURE:
<221> NAME/KEY: VARIANT
<222> LOCATION: 97
<223> OTHER INFORMATION: Xaa = Asp or Glu
<220> FEATURE:
<221> NAME/KEY: VARIANT
<222> LOCATION: 247
<223> OTHER INFORMATION: Xaa = Phe or Tyr
<220> FEATURE:
<221> NAME/KEY: VARIANT
<222> LOCATION: 256
<223> OTHER INFORMATION: Xaa = Asp or Gly
<220> FEATURE:
<221> NAME/KEY: VARIANT
<222> LOCATION: 258
<223> OTHER INFORMATION: Xaa = Asp or Glu
<220> FEATURE:
<221> NAME/KEY: VARIANT
<222> LOCATION: 272
<223> OTHER INFORMATION: Xaa = Lys or Thr

<400> SEQUENCE: 50

Met Pro Ile Arg Val Pro Asp Glu Leu Pro Ala Val Asn Phe Leu Arg
    1               5                   10                  15
```

```
Glu Glu Asn Val Phe Val Met Thr Thr Ser Arg Ala Ser Gly Gln Glu
            20                  25                  30

Ile Arg Pro Leu Lys Val Leu Ile Leu Asn Leu Met Pro Lys Lys Ile
        35                  40                  45

Glu Thr Glu Asn Gln Phe Leu Arg Leu Leu Ser Asn Ser Pro Leu Gln
 50                  55                  60

Val Asp Ile Gln Leu Leu Arg Ile Asp Ser Arg Glu Ser Arg Asn Thr
 65                  70                  75                  80

Pro Ala Glu His Leu Asn Asn Phe Tyr Cys Asn Phe Glu Asp Ile Gln
                85                  90                  95

Xaa Gln Asn Phe Asp Gly Leu Ile Val Thr Gly Ala Pro Leu Gly Leu
                100                 105                 110

Val Glu Phe Asn Asp Val Ala Tyr Trp Pro Gln Ile Lys Gln Val Leu
            115                 120                 125

Glu Trp Ser Lys Asp His Val Thr Ser Thr Leu Phe Val Cys Trp Ala
130                 135                 140

Val Gln Ala Ala Leu Asn Ile Leu Tyr Gly Ile Pro Lys Gln Thr Arg
145                 150                 155                 160

Thr Asp Lys Leu Ser Gly Val Tyr Glu His His Ile Leu His Pro His
                165                 170                 175

Ala Leu Leu Thr Arg Gly Phe Asp Asp Ser Phe Leu Ala Pro His Ser
                180                 185                 190

Arg Tyr Ala Asp Phe Pro Ala Ala Leu Ile Arg Asp Tyr Thr Asp Leu
            195                 200                 205

Glu Ile Leu Ala Glu Thr Glu Glu Gly Asp Ala Tyr Leu Phe Ala Ser
210                 215                 220

Lys Asp Lys Arg Ile Ala Phe Val Thr Gly His Pro Glu Tyr Asp Ala
225                 230                 235                 240

Gln Thr Leu Ala Gln Glu Xaa Phe Arg Asp Val Glu Ala Gly Leu Xaa
                245                 250                 255

Pro Xaa Val Pro Tyr Asn Tyr Phe Pro His Asn Asp Pro Gln Asn Xaa
            260                 265                 270

Pro Arg Ala Ser Trp Arg Ser His Gly Asn Leu Leu Phe Thr Asn Trp
            275                 280                 285

Leu Asn Tyr Tyr Val Tyr Gln Ile Thr Pro Tyr Asp Leu Arg His Met
290                 295                 300

Asn Pro Thr Leu Asp
305
```

```
<210> SEQ ID NO 51
<211> LENGTH: 309
<212> TYPE: PRT
<213> ORGANISM: Artificial Sequence
<220> FEATURE:
<223> OTHER INFORMATION: Sequence logo
<220> FEATURE:
<221> NAME/KEY: VARIANT
<222> LOCATION: 28
<223> OTHER INFORMATION: Xaa = Val or Ala
<220> FEATURE:
<221> NAME/KEY: VARIANT
<222> LOCATION: 29
<223> OTHER INFORMATION: Xaa = Pro or Ser
<220> FEATURE:
<221> NAME/KEY: VARIANT
<222> LOCATION: 63
<223> OTHER INFORMATION: Xaa = Leu or Phe
<220> FEATURE:
<221> NAME/KEY: VARIANT
```

```
<222> LOCATION: 64
<223> OTHER INFORMATION: Xaa = Glu or Gln
<220> FEATURE:
<221> NAME/KEY: VARIANT
<222> LOCATION: 114
<223> OTHER INFORMATION: Xaa = Gly or Glu
<220> FEATURE:
<221> NAME/KEY: VARIANT
<222> LOCATION: 140
<223> OTHER INFORMATION: Xaa = Phe or Pro
<220> FEATURE:
<221> NAME/KEY: VARIANT
<222> LOCATION: 290
<223> OTHER INFORMATION: Xaa = His or Asn

<400> SEQUENCE: 51

Met Pro Ile Arg Val Pro Asp Glu Leu Pro Ala Val Asn Phe Leu Arg
 1               5                  10                  15

Glu Glu Asn Val Phe Val Met Thr Thr Ser Arg Xaa Xaa Gly Gln Glu
             20                  25                  30

Ile Arg Pro Leu Lys Val Leu Ile Leu Asn Leu Met Pro Lys Lys Ile
         35                  40                  45

Glu Thr Glu Asn Gln Phe Leu Arg Leu Leu Ser Asn Ser Pro Xaa Xaa
     50                  55                  60

Val Asp Ile Gln Leu Leu Arg Ile Asp Ser Arg Glu Ser Arg Asn Thr
 65                  70                  75                  80

Pro Ala Glu His Leu Asn Asn Phe Tyr Cys Asn Phe Glu Asp Ile Gln
                 85                  90                  95

Asp Gln Asn Phe Asp Gly Leu Ile Val Thr Gly Ala Pro Leu Gly Leu
            100                 105                 110

Val Xaa Phe Asn Asp Val Ala Tyr Trp Pro Gln Ile Lys Gln Val Leu
        115                 120                 125

Glu Trp Ser Lys Asp His Val Thr Ser Thr Leu Xaa Val Cys Trp Ala
130                 135                 140

Val Gln Ala Ala Leu Asn Ile Leu Tyr Gly Ile Pro Lys Gln Thr Arg
145                 150                 155                 160

Thr Glu Lys Leu Ser Gly Val Tyr Glu His His Ile Leu His Pro His
                165                 170                 175

Ala Leu Leu Thr Arg Gly Phe Asp Asp Ser Phe Leu Ala Pro His Ser
            180                 185                 190

Arg Tyr Ala Asp Phe Pro Ala Ala Leu Ile Arg Asp Tyr Thr Asp Leu
        195                 200                 205

Glu Ile Leu Ala Glu Thr Glu Glu Gly Asp Ala Tyr Leu Phe Ala Ser
210                 215                 220

Lys Asp Lys Arg Ile Ala Phe Val Thr Gly His Pro Glu Tyr Asp Ala
225                 230                 235                 240

Gln Thr Leu Ala Gln Glu Phe Phe Arg Asp Val Glu Ala Gly Leu Asp
                245                 250                 255

Pro Asp Val Pro Tyr Asn Tyr Phe Pro His Asn Asp Pro Gln Asn Thr
            260                 265                 270

Pro Arg Ala Ser Trp Arg Ser His Gly Asn Leu Leu Phe Thr Asn Trp
        275                 280                 285

Leu Xaa Tyr Tyr Val Tyr Gln Ile Thr Pro Tyr Asp Leu Arg His Met
    290                 295                 300

Asn Pro Thr Leu Asp
305
```

MODIFIED POLYPEPTIDE HAVING HOMOSERINE ACETYLTRANSFERASE ACTIVITY AND MICROORGANISM EXPRESSING THE SAME

STATEMENT REGARDING SEQUENCE LISTING

The Sequence Listing associated with this application is provided in text format in lieu of a paper copy, and is hereby incorporated by reference into the specification. The name of the text file containing the Sequence Listing is 200187_415USPC_SEQUENCE_LISTING.txt. The text file is 62.3 KB, was created on Jun. 11, 2014, and is being submitted electronically via EFS-Web.

BACKGROUND OF THE INVENTION

1. Field of the Invention

The present invention relates to a polypeptide that is modified to have homoserine acetyltransferase activity, a polynucleotide encoding the same, a recombinant vector comprising the polynucleotide, a microorganism that is transformed with the recombinant vector, and a method for producing O-acetyl homoserine using the microorganism.

2. Description of the Related Art

Methionine is one of the essential amino acids in the body, and has been widely used as an animal feed and food additive, as well as a component of medical aqueous solutions and other raw materials for medicinal products. Methionine acts as a precursor of choline (lecithin) and creatine, and is also used as a raw material for the synthesis of cysteine and taurine. In addition, it functions as a sulfur donor.

S-adenosyl-methionine is derived from L-methionine and serves as a methyl donor in the body, and it is involved in the synthesis of various neurotransmitters in the brain. Methionine and/or S-adenosyl-L-methionine (SAM) is/are also found to prevent lipid accumulation in the liver and arteries and to be effective for the treatment of depression, inflammation, liver diseases and muscle pain.

Methionine can be chemically or biologically synthesized to be used in animal feed, food and medicines.

In the chemical synthesis, L-methionine is mostly produced by hydrolysis of 5-(β-methylmercaptoethyl)hydantoin. However, the chemically synthesized methionine has a disadvantage of only being produced as a mixed form of L-type and D-type.

With regard to biological synthesis of L-methionine, U.S. Patent Publication No. US2005/0054060A1 describes a method of synthesizing homocysteine or methionine directly using $H_2S$ or $CH_3SH$, while not using cysteine, by modifying cystathionine synthase for the preparation of microorganisms. In this method, modified cystathionine synthase is directly introduced into cells to synthesize methionine according to intracellular methionine synthesizing process. However, there are practical problems in that this method produces only a small amount of methionine because of inhibitory actions of synthesized methionine resulting from using intracellular methionine metabolic pathways, and $H_2S$ or $CH_3SH$ also causes cytotoxicity.

To solve these problems, the present inventors had developed a two-step process of converting L-methionine precursor into L-methionine by enzyme reaction (PCT/KR2007/003650). This two-step process can solve the above problems of cytotoxicity of $H_2S$ or $CH_3SH$ and metabolic process inhibition by produced L-methionine. Moreover, this process is characterized in that it is very efficient to produce only L-methionine selectively, and not a mixed form of D-methionine and L-methionine.

In this two-step process, O-succinyl homoserine and O-acetyl homoserine can be used as the methionine precursor. During conversion reaction of methionine, O-acetyl homoserine is advantageous over O-succinyl homoserine in terms of production yield of precursor to methionine ratio. Specifically, 0.91 mole of methionine can be produced from 1 mole of O-acetyl homoserine whereas only 0.67 mole of methionine can be produced from 1 mole of O-succinyl homoserine. Thus, production cost of the final product methionine can be reduced by using O-acetyl homoserine as the methionine precursor, and high production yield of O-acetyl homoserine is a crucial factor for the mass-production of methionine.

Meanwhile, use of the O-acetyl homoserine or O-succinyl homoserine as the methionine precursor depends on the type of microorganisms. In detail, microorganisms belonging to the genus *Escherichia*, *Enterobacteria*, *Salmonella*, and *Bacillus* produce O-succinyl-homoserine from homoserine and succinyl-coA by L-homoserine O-succinyltransferase (Biochemistry. 1999 Oct. 26; 38(43): 14416-23), and microorganisms belonging to the genus *Corynebacterium*, *Leptospira*, *Deinococcus*, *Pseudomonas*, and *Mycobacterium* produces O-acetyl-homoserine from homoserine and acetyl-coA by L-homoserine O-acetyltransferase (Journal of Bacteriology, March 2002, p. 1277-1286).

Therefore, expression of O-acetyl homoserine transferase by introduction of metX, a foreign gene, is required for the biosynthesis of O-acetyl homoserine using microorganisms of the genus *Escherichia* which are used to produce recombinant proteins for experimental and industrial purposes. However, there are problems related to negative attitudes of consumers toward introduction of foreign genes into microorganisms used for the production of food products, and proving safety of introduction of foreign genes.

Accordingly, the present inventors have made efforts to prepare a strain of the genus *Escherichia* that produces O-acetyl homoserine advantageous in terms of the production yield without introduction of foreign genes. As a result, they found that homoserine succinyltransferase activity can be converted into homoserine acetyltransferase activity by using a modified polypeptide prepared by substituting glutamic acid for amino acid at position 111 of O-succinyl homoserine transferase which is from *E. coli*, thereby completing the present invention.

SUMMARY OF THE INVENTION

An object of the present invention is to provide a modified polypeptide, in which the polypeptide having homoserine O-succinyltransferase activity is converted to have homoserine acetyltransferase activity.

Another object of the present invention is to provide a polynucleotide encoding the above modified polypeptide.

Still another object of the present invention is to provide a recombinant vector comprising polynucleotide sequences operably linked to the above polynucleotide.

Still another object of the present invention is to provide a microorganism comprising the above polynucleotide.

Still another object of the present invention is to provide a microorganism that is transformed to the recombinant vector operably linked to the above polynucleotide.

Still another object of the present invention is to provide a method for producing O-acetyl homoserine using the microorganism that expresses the modified polypeptide having homoserine acetyltransferase activity.

DETAILED DESCRIPTION OF THE PREFERRED EMBODIMENTS

In one aspect to achieve the above objects, the present invention provides a modified polypeptide having homoserine O-acetyltransferase activity having the amino acid sequence of SEQ ID No. 17 or at least 95% homologous thereto, in which the amino acid at position 111 from the start point amino acid, methionine, of the sequence is substituted with glutamic acid.

As used herein, the polypeptide having homoserine O-succinyltransferase activity means a polypeptide having an activity of synthesizing O-succinyl homoserine from homoserine and succinyl-coA present in the methionine biosynthetic pathways, as shown in the following Reaction Scheme.

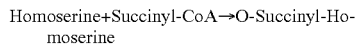

The polypeptide having homoserine O-succinyltransferase activity may be a recombinant polypeptide which is from a microorganism of the genus Enterobacteria, Salmonella, Pseudomonas, Bacillus, or Escherichia, preferably, a recombinant polypeptide having homoserine succinyltransferase activity which is from a microorganism of the genus Escherichia, and more preferably, a recombinant polypeptide having homoserine O-succinyltransferase activity which is from E. coli.

In the present invention, the polypeptide having homoserine O-succinyltransferase activity may include a polypeptide having homoserine succinyltransferase activity that is composed of the amino acid sequence of SEQ ID NO: 17 or at least 95% homologous thereto, as long as it has the activity shown in the above Reaction Scheme.

Figure 1:
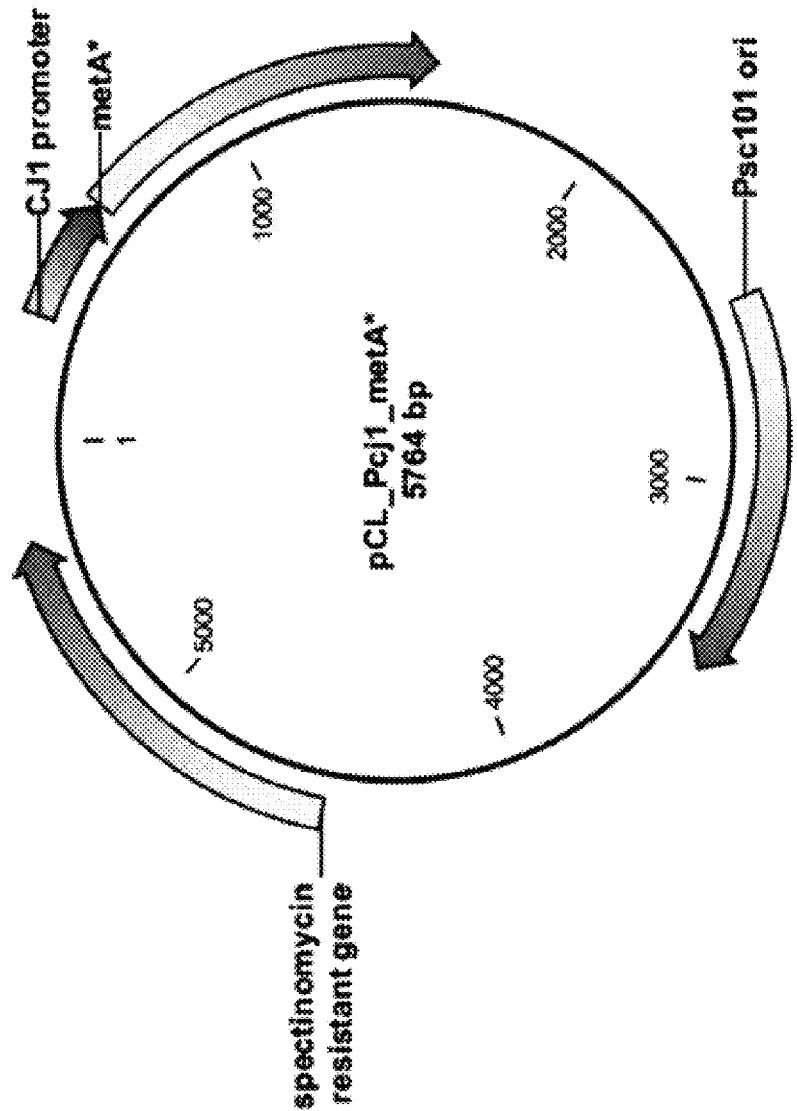
FIG. 1 is a diagram showing a recombinant vector that is operably linked to a polynucleotide encoding the modified polypeptide according to the present invention.
Figure 2A:
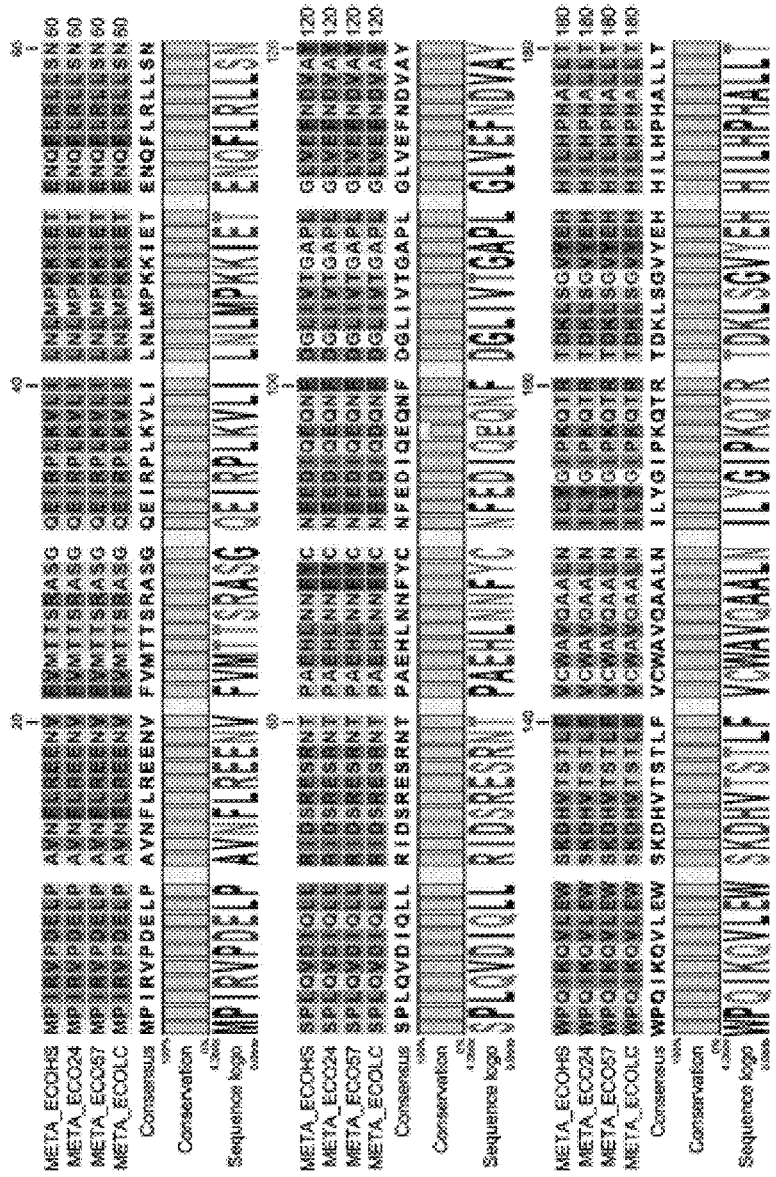
FIGS. 2a and 2b show homology comparison of the primary amino acid sequences of homoserine O-succinyltransferase between E. coli variants; META_ECOHS (SEQ ID NO: 41), META_ECO24 (SEQ ID NO: 42, META_ECO57 (SEQ ID NO: 43), META_ECOLC (SEQ ID NO: 45), consensus (SEQ ID NO: 49), sequence logo (SEQ ID NO: 50).
Figure 2B:
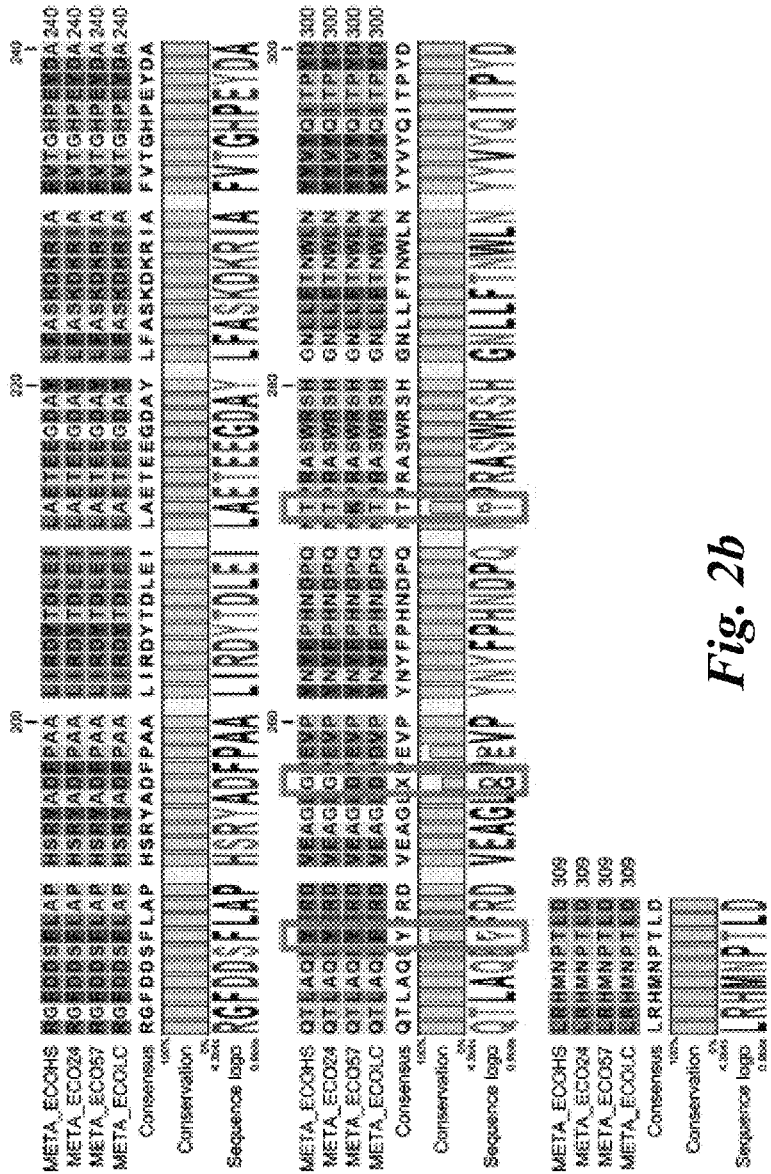
Figure 3A:
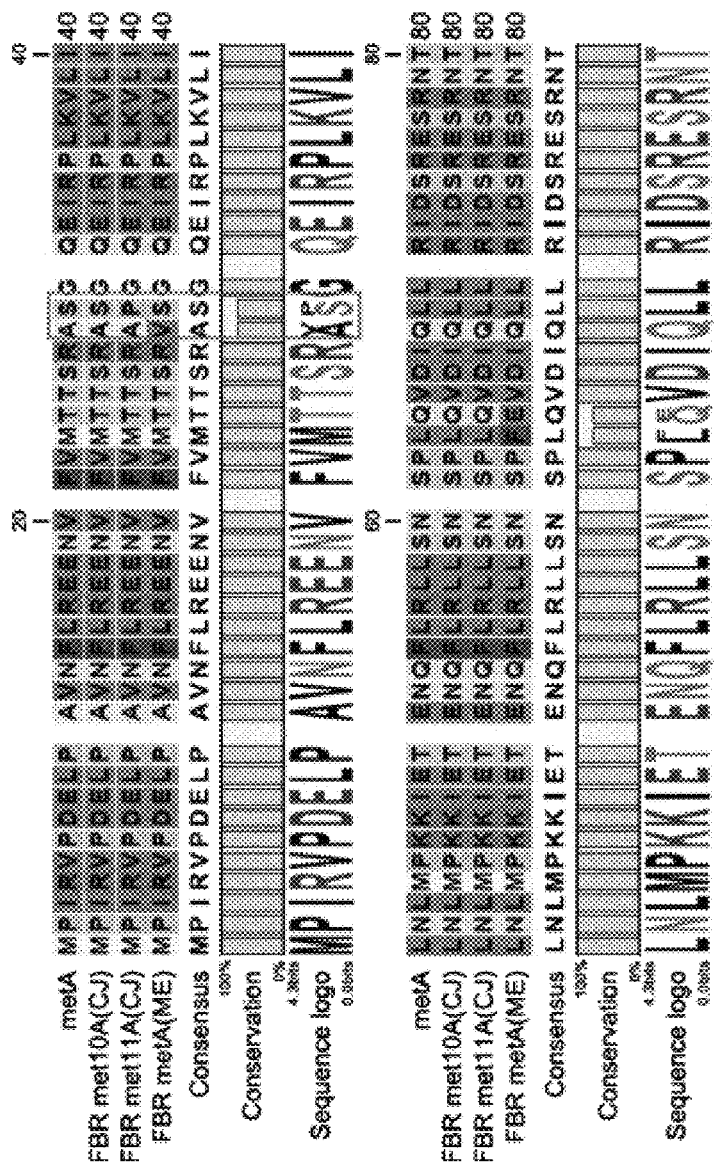
FIGS. 3a, 3b, 4a and 4b show homology comparisons of the primary amino acid sequences of mutant homoserine O-succinyltransferase (met A (SEQ ID NO: 17), FBR met10A (CJ) (SEQ ID NO:46), FBR met11A(CJ) (SEQ ID NO: 47), FBR metA(ME) (SEQ ID NO: 48), consensus (SEQ ID NO: 46), sequence logo (SEQ ID NO: 51)) resistant to feedback regulation by methionine, in which the primary amino acid sequences of the wild-type homoserine O-succinyltransferase, the feedback regulation-resistant mutant homoserine O-succinyltransferase met10A and met11A disclosed in PCT Publication No. WO 2008/127240, and the feedback regulation-resistant mutant homoserine O-succinyltransferase disclosed in PCT Publication No. WO 2005/108561 were used for comparison.
Figure 3B:
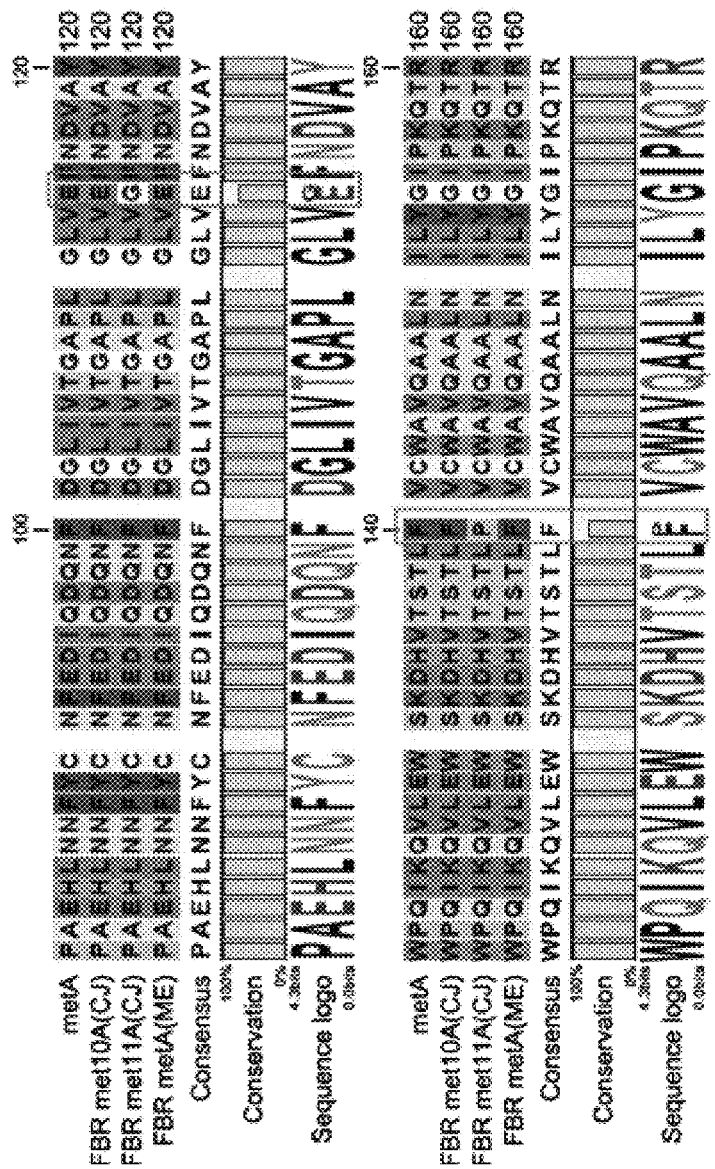
Figure 4A:
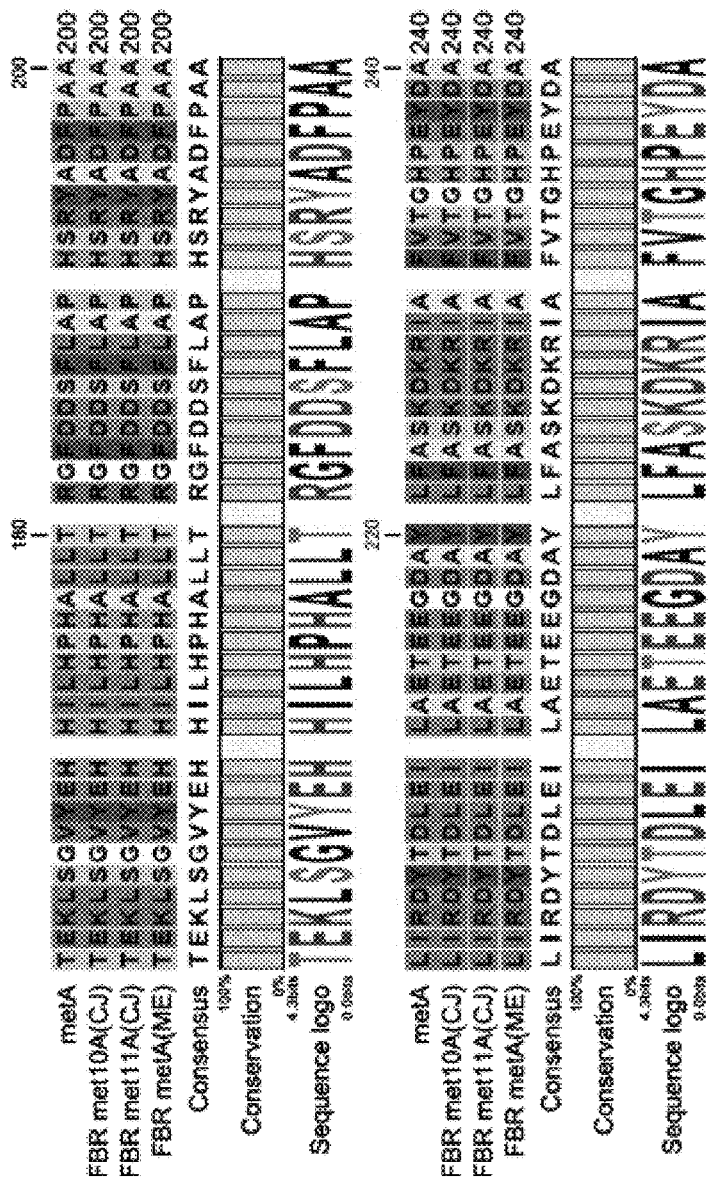
Figure 4B:
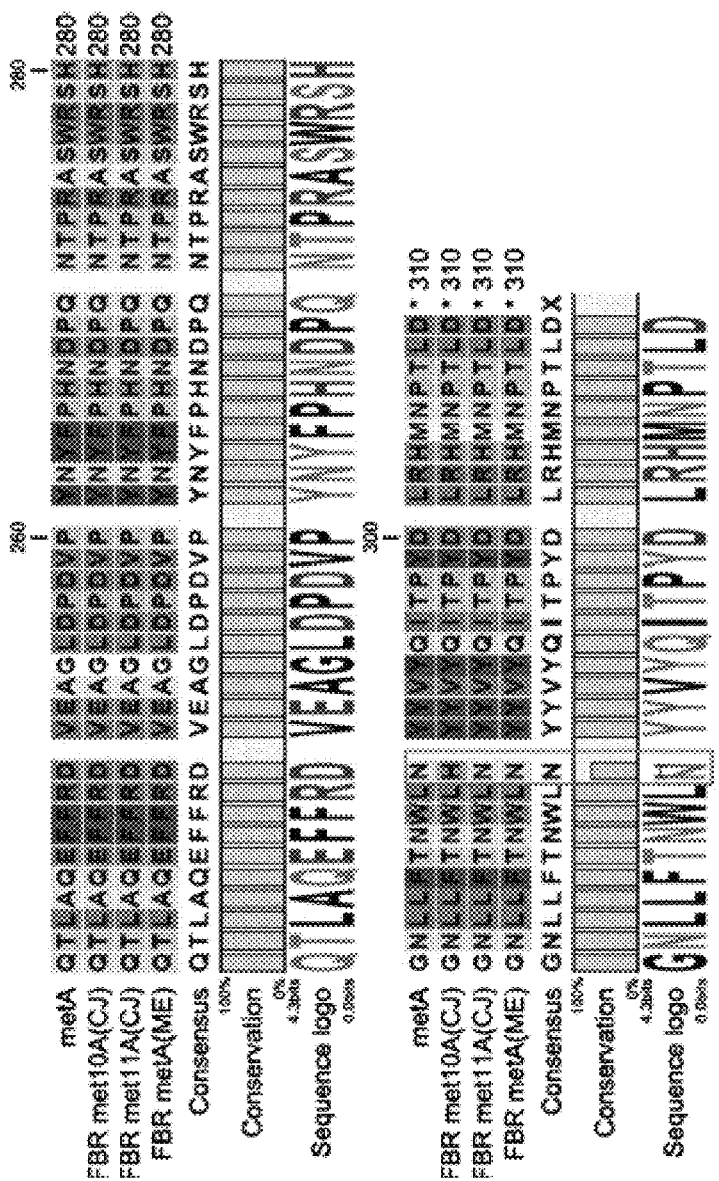

In Examples of the present invention, the homology of the amino acid sequences of homoserine O-succinyltransferase between different species of E. coli was compared. As a result, there was less than 5% variation in the homoserine O-succinyltransferase polypeptides between different species of E. coli (that is, they have at least 95% homology), but there was no significant difference in the homoserine O-succinyltransferase activity (FIGS. 2a and 2b). These results indicate that the polypeptides having 95% or more homology to the polypeptide of SEQ ID NO: 17 of the present invention also have identical homoserine O-succinyltransferase activity, which is apparent to those skilled in the art and is visualized by the present inventors.

As used herein, the term "modified polypeptide" means a polypeptide having homoserine O-acetyltransferase activity by substituting a part of the amino acid sequences of the polypeptide having homoserine O-succinyltransferase activity, unlike the wild-type. That is, the modified polypeptide of the present invention means a modified polypeptide having the same activity as in the following Reaction Scheme, which has substrate specificity for acetyl-coA rather than succinyl-coA by substituting a part of the amino acid sequences of the polypeptide having homoserine O-succinyltransferase activity.

In the present invention, the above modified polypeptide may be a modified polypeptide in which the amino acid at position 111 of a polypeptide having amino acid sequence of SEQ ID NO: 17 or a polypeptide having 950 or more sequence homology thereto is substituted with glutamic acid (SEQ ID NO.: 18), and the amino acid at position 112 of the polypeptide is further substituted with threonine (SEQ ID NO: 19) or histidine (SEQ ID NO: 20).

The further substitution of threonine or histidine for the amino acid leucine at position 112 was found to enhance homoserine acetyltransferase activity (Tables 2 and 3).

According to one preferred embodiment, the above modified polypeptide may be a polypeptide having any one of the amino acid sequences of SEQ ID NOs: 18 to 20.

In Examples of the present invention, a plasmid capable of expressing a polypeptide wherein the amino acid glycine at position 111 of a homoserine succinyltransferase encoded by metA gene of E. coli composed of the nucleotide sequence represented by SEQ ID NO: 39 is substituted with glutamic acid and a plasmid capable of expressing a polypeptide wherein the amino acid at position 112 in addition to the above substitution, is substituted with threonine or histidine are prepared (Example 2).

Further, Experimental Examples of the present invention showed that only O-succinyl homoserine was produced by CJM2 pCL_Pcj1_metA(wt) and CJM3 pCL_Pcj1_metA(wt) transformed with a plasmid including the wild type metA gene (SEQ ID NO: 39). In contrast, only O-acetyl homoserine was accumulated by a strain that is transformed with a plasmid including the gene encoding the modified polypeptide of the present invention (Experimental Example 2, Tables 2 and 3).

Therefore, a microorganism expressing the modified polypeptide of the present invention is advantageous in that it is able to produce O-acetyl homoserine as a methionine precursor capable of high yield production without introduction of foreign genes for homoserine acetyltransferase activity.

In the present invention, the above modified polypeptide may be resistant to feedback regulation by methionine resulting from substitution of a part of the amino acids of the polypeptide having homoserine succinyltransferase activity. That is, most activity of homoserine succinyltransferase is regulated through feedback inhibition by a small amount of methionine in a medium, and thus the modified polypeptide of the present invention may be resistant to feedback regulation by methionine for the mass-production of O-acetyl homoserine.

In the present invention, the amino acid substitution to avoid the feedback regulation by methionine may be performed according to the method disclosed in PCT Publication No. WO 2008/127240. In detail, the feedback regulation by methionine may be avoided by substitution of proline for the amino acid at position 29, substitution of glycine for the amino acid at position 114, substitution of serine for the amino acid at position 140 of the polypeptide having homoserine succinyltransferase activity, or one or more combinations of the three amino acid substitutions. Preferably, two or more, and most preferably three amino acids may be substituted.

According to one preferred embodiment, the modified polypeptide resistant to feedback regulation by methionine may be a modified polypeptide having any one amino acid sequence selected from the amino acid sequences of SEQ ID NOs: 21 to 23.

In Examples of the present invention, the amino acids at position 29, 114 and 140 of the recombinant polypeptide having homoserine succinyltransferase activity that is encoded by metA gene of *E. coli* were substituted by proline, glycine, and serine, respectively so as to avoid feedback regulation by methionine. In addition, constructed were plasmids including polynucleotides encoding modified polypeptides having homoserine acetyltransferase activity, which are [pCL_Pcj1_metA#11(EL)] prepared by substitution of glutamic acid for the amino acid at position 111, [pCL_Pcj1_metA#11(ET)] prepared by substitution of glutamic acid and threonine for the amino acids at position 111 and 112, and [pCL_Pcj1_metA#11(EH)] prepared by substitution of glutamic acid and histidine for the amino acids at position 111 and 112(Example 3).

Further, Experimental Examples of the present invention showed that among the strains expressing modified polypeptides resistant to feedback regulation by methionine, CJM2 pCL_Pcj1_metA(#11)EH and CJM3 pCL_Pcj1_metA(#11)EH strains prepared by substitution of glutamic acid and histidine for the amino acids at position 111 and 112 showed high O-acetyl homoserine productivities of 11.1 g/L and 24.8 g/L, respectively, and these accumulations of O-acetyl homoserine are similar to those by introduction of foreign homoserine acetyltransferase gene (Experimental Example 2, Tables 2 and 3).

In another aspect, the present invention provides a polynucleotide encoding the modified polypeptide, or a recombinant vector comprising polynucleotide sequences operably linked to the polynucleotide.

In the present invention, the above polynucleotide is a nucleotide polymer composed of nucleotide monomers covalently bonded in a chain, and examples thereof are DNA or RNA strands having a predetermined or longer length, and it is a polynucleotide encoding the above modified polypeptide.

In the present invention, the above polynucleotide may be a polynucleotide having any one of the nucleotide sequences of SEQ ID NOs: 24 to 29.

As used herein, the above term "recombinant vector" is a means for expressing the modified polypeptide by introduction of DNA into a host cell in order to prepare a microorganism expressing the modified polypeptide of the present invention, and the known expression vectors such as plasmid vector, a cosmid vector, and a bacteriophage vector may be used. The vector may be easily prepared by those skilled in the art according to any known method using recombinant DNA technology.

In the present invention, the recombinant vector may be a pACYC177, pACYC184, pCL1920, pECCG117, pUC19, pBR322, or pMW118 vector, and preferably the pCL1920 vector.

The term "operably linked" means that an expression regulatory sequence is linked in such a way of regulating the transcription and translation of a polynucleotide sequence encoding the modified polypeptide, and includes maintaining a precise translation frame in such a way that the modified polypeptide encoded by the polynucleotide sequence is produced when the polynucleotide sequence is expressed under the control of regulatory sequences (including a promoter).

In still another aspect, the present invention provides a microorganism comprising the polynucleotide encoding the above modified polypeptide and a microorganism that is transformed with the recombinant vector operably linked to the polynucleotide encoding the above modified polypeptide.

As used herein, the term "transformation" means a method that a gene is introduced into a host cell to be expressed in the host cell. The transformed gene, if it is in the state of being expressed in the host cell, may be inserted in the chromosome of the host cell or may exist independent of the chromosome.

In addition, the gene includes DNA and RNA as a polynucleotide capable of encoding a polypeptide. The gene can be introduced in any type, as long as it can be introduced in the host cell and expressed therein. For example, the gene may be introduced into the host cell in the type of expression cassette which is a polynucleotide construct including whole elements for expressing the gene by itself. Typically, the expression cassette includes a promoter, a transcription termination signal, a ribosome binding site and a translation termination signal, which are operably linked to the gene. The expression cassette may be in the type of the expression vector capable of self-replication. The above gene may also be introduced into the host cell by itself or in the type of polynucleotide construct so as to be operably linked to the sequence required for expression in the host cell.

The above microorganism is a prokaryotic or eukaryotic microorganism that is able to express the modified polypeptide by including the polynucleotide encoding the modified polypeptide or by transformation with the recombinant vector operably linked to the polynucleotide encoding the modified polypeptide, and for example, it may be a microorganism belonging to the genus *Escherichia, Bacillus, Aerobacter, Serratia, Providencia, Erwinia, Schizosaccharomyces, Enterobacteria, Zygosaccharomyces, Leptospira, Deinococcus, Pichia, Kluyveromyces, Candida, Hansenula, Debaryomyces, Mucor, Torulopsis, Methylobacter, Salmonella, Streptomyces, Pseudomonas, Brevibacterium* or *Corynebacterium*.

In the present invention, the the microorganism is expressing the polypeptide having homoserine O-succinyltransferase activity. For example, it may be a microorganism belonging to the genus *Bacillus, Escherichia, Enterobacteria*, or *Salmonella*, preferably a microorganism belonging to the genus *Escherichia*, and more preferably, *E. coli*.

In Examples of the present invention, prepared were *E. coli* CJM2 pCL_Pcj1_metAEL, CJM2 pCL_Pcj1_metAET, and CJM2 pCL_Pcj1_metAEH strains transformed with the recombinant vector comprising the polynucleotide encoding the modified polypeptide of the present invention (Example 2 and Experimental Example 2), and *E. coli* CJM2 pCL_Pcj1_metA(#11)EL, CJM2 pCL_Pcj1_metA(#11)ET, and CJM2 pCL_Pcj1_metA(#11)EH strains transformed with the recombinant vector including the polynucleotide encoding the modified polypeptide resistant to feedback regulation by methionine and having homoserine O-acetyltransferase activity of the present invention (Example 3 and Experimental Example 2). Among the above strains, the CJM2 pCL_Pcj1_metA(#11)EL, CJM2 pCL_Pcj1_metA(#11)ET, and CJM2 pCL_Pcj1_metA(#11)EH strains were designated as CA05-0546, CA05-0547 and CA05-0548, respectively and deposited in the Korean Culture Center of Microorganism on Dec. 14, 2010, and assigned the accession numbers, KCCM11145P, KCCM11146P and KCCM11147P, respectively.

The present invention provides the modified polypeptide having homoserine O-acetyltransferase activity, in which a part of the amino acid sequences of the polypeptide having homoserine O-succinyltransferase activity is substituted. Thus, it is advantageous in that when the modified polypeptide of the present invention is expressed in the microorganism expressing the polypeptide having homoserine O-succinyltransferase activity only, the polypeptide having homoserine O-acetyltransferase activity can be expressed without introduction of a foreign gene such as metX encoding homoserine O-acetyltransferase.

In the present invention, the above microorganism may be a microorganism that is additionally modified to have enhanced acetyl-CoA synthetase activity or additionally modified to have pantothenate kinase activity resistant to feedback inhibition by CoA accumulation, in order to produce a large amount of O-acetyl homoserine.

In the present invention, acetyl-CoA synthetase and pantothenate kinase which are from various microorganisms, and genes encoding the proteins having these activities are commonly called acs and coaA, respectively.

In the present invention, the enhancement of acetyl-CoA synthetase activity may be achieved through enhancement of gene expression by modification of nucleotide sequences of the promoter region and the 5'-UTR region of the acs gene encoding acetyl-CoA synthetase, and the activity of the protein can be enhanced by introducing the mutation in the ORF region of the corresponding gene, and the protein expression level can be enhanced by the introduction of the extra copy of the corresponding gene on the chromosome, or by the introduction of the corresponding gene with the self-promoter or enhanced other promoter in the strain.

More specifically, the acetyl-CoA synthetase activity may be enhanced through substitution of activity-enhanced promoter, induction of promoter mutation for enhancement of the activity, or an increase in the gene copy number, and therefore, the present invention provides a method for improving O-acetyl homoserine productivity, and *E. coli* prepared by the method. For the substitution of activity-enhanced promoter, pTac, pTrc, pPro, pR, and pL, which are known to have enhanced activity, may be used.

According to one preferred embodiment, the present invention provides an O-acetyl homoserine-producing strain, in which the acs gene involved in acetyl-CoA biosynthesis is overexpressed by substituting a constitutive expressing promoter, pro promoter, for its promoter. The pro promoter may be a part or the entire of SEQ ID NO: 30.

The present invention further provides a microorganism that is introduced with a modified pantothenate kinase resistant to feedback inhibition by CoA accumulation in the CoA biosynthetic pathways. More specifically, the amino acid arginine at position 106 in the amino acid sequence of the pantothenate kinase is substituted by alanine (SEQ ID NO: 40) so that it becomes resistant to feedback inhibition by CoA accumulation, leading to improvement of O-acetyl homoserine productivity.

In the present invention, the above microorganism may be a microorganism, in which the copy number of one or more genes selected from the group consisting of phosphoenolpyruvate carboxylase-encoding gene (ppc), aspartate aminotransferase-encoding gene (aspC), and aspartate semialdehyde dehydrogenase encoding-gene (asd) is increased, or the promoter of the gene is replaced by an activity-enhanced promoter or is mutated to have enhanced activity.

In the present invention, the series of enzymes have the activities of synthesizing O-acetyl homoserine from phosphoenolpyruvate, as shown in the following Reaction Schemes. Therefore, accumulation of O-acetyl homoserine in cells can be induced by enhancing expression of the genes having these activities.

Phosphoenolpyruvate carboxylase (ppc)

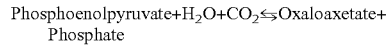

Aspartate aminotransferase (aspC)

Aspartate kinase (thrA)

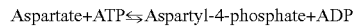

Aspartate semialdehyde dehydrogenase (asd)

Homoserine dehydrogenase (thrA)

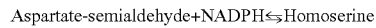

In Reaction Schemes, the thrA gene encoding the bifunctional enzyme, aspartate kinase/homoserine dehydrogenase is previously enhanced through relief of feedback inhibition in the CJM2 strain in Experimental Example 2, and the rest three enzymes can be enhanced through an increase in the gene copy number, substitution of promoter of the above gene to activity-enhancing promoter, or induction of promoter mutation for enhancement of the activity.

As used herein, the term "increase in the copy number" means additional introduction of a desired gene into the chromosome or by introduction of a plasmid having the gene encoding the corresponding enzyme.

In Examples of the present invention, a CJM2-AP strain was prepared by deletion of the acs promoter of a metA and metB-deleted CJM2 strain and substitution of the pro promoter therefor, and then transformed to have feedback resistant coaA so as to prepare a CJM2-AP/CO strain having increased Acetyl-coA pool, followed by preparation of a CJM3 strain having two copies of three ppc, aspC, and asd genes. Thereafter, pCL_Pcj1_metA#11(EL), pCL_Pcj1_metA#11(EH) and pCL_Pcj1_metA#11(ET)-introduced CJM3 strains were designated as CA05-0578, CA05-0579 and CA05-0580, respectively and deposited in the Korean Culture Center of Microorganism on Dec. 12, 2011, and assigned the accession numbers, KCCM11228P, KCCM11229P and KCCM11230P, respectively (Experimental Example 2).

In still another aspect, the present invention provides a method for producing O-acetyl homoserine, comprising the steps of culturing the microorganism comprising the polynucleotide encoding the modified polypeptide or the microorganism that is transformed with the recombinant vector operably linked to the polynucleotide encoding the modified polypeptide, and obtaining O-acetyl homoserine that is produced during the above cultivation of the microorganism.

In the present invention, production of O-acetyl homoserine using the microorganism expressing the modified polypeptide may be performed with a proper medium and conditions known in the art. It is well understood by those skilled in the art that the culture method may be easily adjusted according to the selected strain.

Examples of the culture method include, but not limited to, batch, continuous and fed-batch culture. The medium used in the cultivation has to meet the culture conditions for a specific strain.

The medium used in the present invention may include any one carbon source of sucrose, glucose, glycerol, and acetic acid or combinations thereof, and the nitrogen source to be used is exemplified by organic nitrogen sources such as peptone, yeast extract, beef extract, malt extract, corn steep liquor, and bean flour, and inorganic nitrogen sources such as urea, ammonium sulfate, ammonium chloride, ammonium phosphate, ammonium carbonate, and ammonium nitrate or combinations thereof.

The medium may include potassium dihydrogen phosphate, dipotassium hydrogen phosphate and corresponding sodium-containing salts as a phosphate source. The medium may also include a metal salt such as magnesium sulfate or iron sulfate. In addition, amino acids, vitamins and proper precursors may be added as well. The medium or the precursors may be added to the culture by batch-type or continuous type. pH of the culture may be adjusted during the cultivation by adding appropriately a compound such as ammonium hydroxide, potassium hydroxide, ammonia, phosphoric acid and sulfuric acid, and the generation of foams may be inhibited during the cultivation by using an antifoaming agent such as fatty acid polyglycol ester.

In order to maintain aerobic conditions of the culture, oxygen or oxygen-containing gas may be injected into the culture. In order to maintain anaerobic and microaerobic conditions, no gas may be injected or nitrogen, hydrogen, or carbon dioxide may be injected. The temperature of the culture may be 27° C. to 37° C., and preferably 30° C. to 35° C. The period of cultivation may be continued as long as the desired material is produced, and preferably for 10 to 100 hours.

Hereinafter, the present invention will be described in more detail with reference to Examples and Experimental Examples. However, these Examples are for illustrative purposes only, and the invention is not intended to be limited by these Examples.

Example 1

Construction of Plasmid Including Homoserine O-Succinyltransferase and Homoserine O-Acetyltransferase PCR was performed using the chromosome of *E. coli* W3110 strain (Accession No. ATCC9637) purchased from American Type Culture Collection as a template and primers of SEQ ID NO: 1 and SEQ ID NO: 2 to amplify the metA gene encoding homoserine O-succinyltransferase.

The primers used in PCR were prepared based on the sequence of *E. coli* chromosome of NC_000913 registered in NIH Gene Bank, and the primers of SEQ ID NO: 1 and SEQ ID NO: 2 have EcoRV and HindIII restriction sites, respectively.

<SEQ ID NO: 1>
5' AATTGATATCATGCCGATTCGTGTGCCGG 3'

<SEQ ID NO: 2>
5' AATTAAGCTTTTAATCCAGCGTTGGATTCATGTG 3'

PCR was performed using the chromosome of *Deinococcus radiodurans* as a template and primers of SEQ ID NO: 3 and SEQ ID NO: 4 to amplify the metX gene encoding homoserine O-acetyltransferase (SEQ ID NO: 44). The primers of SEQ ID NO: 3 and SEQ ID NO: 4 have EcoRV and HindIII restriction sites, respectively.

<SEQ ID NO: 3>
5' AATTGATATCATGACCGCCGTGCTCGC 3'

<SEQ ID NO: 4>
5' AATTAAGCTTTCAACTCCTGAGAAACGCCCC 3'

PCR was performed under the following conditions: denaturation at 94° C. for 3 minutes, 25 cycles consisting of denaturation at 94° C. for 30 seconds, annealing at 56° C. for 30 seconds, and polymerization at 72° C. for 5 minutes, and polymerization at 72° C. for 7 minutes.

The obtained PCR products were cloned into pCL1920 plasmid containing cj1 promoter (KR 2006-0068505) after treatment of restriction enzymes, EcoRV and HindIII, respectively. *E. coli* DH5α was transformed with the cloned plasmids, and the transformed *E. coli* DH5α was selected on LB plates containing 50 μg/ml of spectinomycin so as to obtain plasmids. The obtained plasmids were designated as pCL_Pcj1_metA and pCL_Pcj1_metXdr, respectively.

Example 2

Construction of Modified Polypeptide Having Homoserine O-Acetyltransferase Activity The amino acid glycine (Gly) at position 111 of O-succinyltransferase was substituted by glutamic acid (Glu) using the pCL_Pcj1_metA plasmid prepared in Example 1 as a template and a site directed mutagenesis kit (Stratagene, USA) (G111E). The sequences of the used primers are as follows:

<SEQ ID NO: 5>
5' ttgtaactggtgcgccgctggaactggtggggtttaatgatgtc 3'

<SEQ ID NO: 6>
5' gacatcattaaacccaccagttccagcggcgcaccagttacaa 3'

The constructed plasmid containing the mutant G111E metA gene was designated as pCL_Pcj1_metA(EL).

In addition, the amino acid glycine (Gly) at position 111 of O-succinyltransferase was substituted by glutamic acid (Glu), and the amino acid leucine at position 112 of O-succinyltransferase was substituted by threonine (L112T) or histidine (L112H). At this time, the sequences of the used primers are as follows:

Substitution of threonine for leucine

<SEQ ID NO: 7>
5' tgtaactggtgcgccgctggaaaccgtggggtttaatgatgtcg 3'

<SEQ ID NO: 8>
5' cgacatcattaaacccacggtttccagcggcgcaccagttaca 3'

Substitution of histidine for leucine

<SEQ ID NO: 9>
5' tgtaactggtgcgccgctggaacatgtggggtttaatgatgtcg 3'

<SEQ ID NO: 10>
5' cgacatcattaaacccacatgttccagcggcgcaccagttaca 3'

Among the constructed plasmids, the plasmid containing the metA gene, in which the amino acid glycine at position 111 was substituted by glutamic acid and the amino acid leucine at position 112 was substituted by threonine, was designated as pCL_Pcj1_metA(ET). Also, the plasmid containing the metA gene, in which the amino acid glycine at position 111 was substituted by glutamic acid and the amino acid leucine at position 112 was substituted by histidine, was designated as pCL_Pcj1_metA(EH).

Example 3

Construction of Feedback-Resistant Modified Polypeptide Having Homoserine O-Acetyltransferase Activity The metA gene having a resistance to feedback regulation by methionine (metA #11) was constructed using the pCL_Pcj1_metA plasmid prepared in Example 2 as a template in the same manner as in Example 2. Specifically, according to the method disclosed in PCT Publication No. WO 2008/127240, serine, glutamic acid, and phenylalanine at position 29, 114, and 140 of O-succinyltransferase were substituted by proline (S29P), glycine (E114G), and serine (F140S), respectively. The sequences of the used primers are as follows.

Substitution of proline for serine

<SEQ ID NO: 11>
5' ATGACAACTTCTCGTGCGCCTGGTCAGGAAATTCG 3'

<SEQ ID NO: 12>
5' CGAATTTCCTGACCAGGCGCACGAGAAGTTGTCAT 3'

Substitution of glycine for glutamic acid

<SEQ ID NO: 13>
5' CGCCGCTGGGCCTGGTGGGGTTTAATGATGTCGCT 3'

<SEQ ID NO: 14>
5' AGCGACATCATTAAACCCCACCAGGCCCAGCGGCG 3'

Substitution of serine for phenylalanine

<SEQ ID NO: 15>
5' CACGTCACCTCGACGCTGAGTGTCTGCTGGGCGGT 3'

<SEQ ID NO: 16>
5' ACCGCCCAGCAGACACTCAGCGTCGAGGTGACGTG 3'

Each of the mutations was sequentially introduced to construct a plasmid containing the metA(#11) gene with the three mutations, which was designated as pCL_Pcj1_metA#11.

Subsequently, constructed were plasmids for expressing polypeptides having mutations identical to those of the modified polypeptides having homoserine O-acetyltransferase activity of Example 2 using the prepared pCL_Pcj1_metA#11 plasmid as a template.

Among the constructed plasmids, the plasmid containing the metA #11 gene, in which the amino acid glycine at position 111 was substituted by glutamic acid, was designated as pCL_Pcj1_metA#11(EL), the plasmid containing the metA #11 gene, in which the amino acid glycine at position 111 was substituted by glutamic acid and the amino acid leucine at position 112 was substituted by threonine, was designated as pCL_Pcj1_metA#11(ET), and the plasmid containing the metA #11 gene, in which the amino acid glycine at position 111 was substituted by glutamic acid and the amino acid leucine at position 112 was substituted by histidine, was designated as pCL_Pcj1_metA#11(EH).

Experimental Example 1

Homology Comparison Between *E. coli* Homoserine Succinyltransferase and Feedback-Resistant *E. coli* Homoserine Succinyltransferase The primary amino acid sequences [SEQ ID NO: 41, SEQ ID NO: 42, and SEQ ID NO: 43 in order] of homoserine O-succinyltransferase of *E. coli* O9:H4 (strain HS), *E. coli* O139: H28 (strain E24377A), and *E. coli* O157:H7 (strain ATCC8739) variants were compared using CLC Main Workbench (CLC bio, Denmark) program.

As shown in FIGS. 2a and 2b, less than 5% variations were observed in the primary amino acid sequences of homoserine O-succinyltransferase of the *E. coli* variants (FIGS. 2a and 2b).

The primary amino acid sequences of the mutant homoserine O-succinyltransferase resistant to feedback regulation by methionine were also compared using the above program. For comparison, the primary amino acid sequences of the wild-type homoserine O-succinyltransferase, the feedback regulation-resistant mutant homoserine O-succinyltransferase met10A and met11A disclosed in PCT Publication No. WO 2008/127240, and the feedback regulation-resistant mutant homoserine O-succinyltransferase disclosed in PCT Publication No. WO 2005/108561 were used.

As shown in FIGS. 3a, 3b, 4a and 4b, less than 5% variations were observed in the primary amino acid sequences of the mutant homoserine O-succinyltransferase resistant to feedback regulation by methionine (FIGS. 3a, 3b, 4a and 4b).

These results indicate that the homoserine O-succinyltransferase polypeptides present in *E. coli* had 950 or higher homology therebetween, and there was no great difference in homoserine succinyltransferase activity even though less than 50 of sequence difference.

Experimental Example 2

Comparison of Substrate Specificity and Activity Between Modified Polypeptides Having Homoserine Acetyltransferase Activity 2-1: Preparation of Test Strains
2-1-1) Deletion of metA and metB Genes
In order to compare activities of modified polypeptides producing excessive amounts of O-acetyl homoserine, a strain accumulating homoserine and having a deletion of O-acetyl homoserine utilization was prepared. The metA and metB gene-deleted strain was prepared by the methods of Examples 1-1 to 1-4 described in Publication Patent EP2108693A2, based on the threonine-producing strain, FTR2533 (KCCM 10541) described in PCT/KR2005/00344. The strain was designated as CJM2. CJM2 is a strain that accumulates a large amount of homoserine and produces O-acetyl homoserine or O-succinyl homoserine depending on the gene introduced.

2-1-2) Substitution of Acs Promoter

Figure 5:
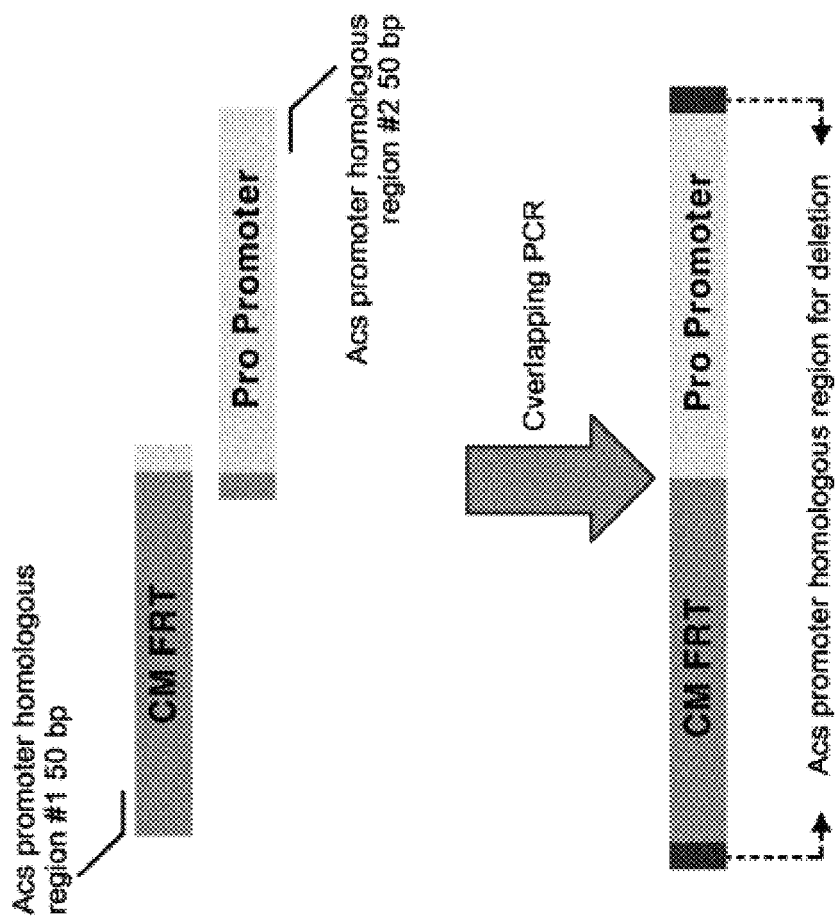
FIG. 5 is a diagram showing the preparation of a FRT-one step deletion cassette by overlapping PCR in order to substitute the pro promoter for the acs promoter in the chromosome.

For the production of excessive amount of O-acetyl homoserine, production of homoserine and acetyl-CoA must be facilitated. First, to facilitate the supply of acetyl-coA, the promoter of acs (acetyl-coA synthetase) gene was replaced by the constitutive pro promoter of SEQ ID NO: 30 so as to induce constitutive overexpression of the desired gene. For substitution of the promoter, modified FRT-one-step PCR was performed (PNAS (2000) vol. 97: 6640-6645). In order to prepare a cassette as shown in FIG. 5, a pKD3 (PNAS (2000) vol. 97: 6640-6645)-derived chloramphenicol resistance FRT cassette was subjected to PCR using SEQ ID NO: 31 and SEQ ID NO: 33, and the pro promoter region was subjected to PCR using SEQ ID NO: 32 and SEQ ID NO: 34. Two PCR products were subjected to overlapping PCR to prepare a single cassette (acs promoter deleted-pro promoter substituted cassette) (Nucleic Acids Res. 1988 Aug. 11; 16(15): 7351-7367). PCR was performed under the following conditions: 30 cycles consisting of denaturation at 94° C. for 30 seconds, annealing at 55° C. for 30 seconds, and polymerization at 72° C. for 1 minute.

<SEQ ID NO: 31>
5' AGGGGCTTCATCCGAATTGCGCCATTGTTGCAATGGCGGTGCTGGAGCTGCTTCGAAGTTC 3'

<SEQ ID NO: 32>
5' GATATTCATATGGACCATGGCTCGAGCATAGCATTTTTATCC 3'

<SEQ ID NO: 33>
5' GGATAAAAATGCTATGCTCGAGCCATGGTCCATATGAATATC 3'

<SEQ ID NO: 34>
5' CGATGTTGGCAGGAATGGTGTGTTTGTGAATTTGGCTCATATGTACCTTTCTCCTCTTTA 3'

The resulting PCR product was electrophoresed on a 1.00 agarose gel, and then DNA was purified from a band of approximately 1.2 kbp. The recovered DNA fragment was electroporated into the CJM2 strain previously transformed with a pKD46 vector (PNAS (2000) vol. 97: 6640-6645). Before electroporation, the CJM2 strain transformed with pKD46 was cultivated at 30° C. in LB medium containing 100 μg/L of ampicillin and 5 mM of L-arabinose until OD600 reached 0.6. Then, the cultured strain was washed once with sterilized distilled water and twice with 10% glycerol. Electroporation was performed at 2500 V. The recovered strain was streaked on LB plate medium containing 25 μg/L of chloramphenicol, followed by cultivation at 37° C. overnight. Then, a strain exhibiting resistance to chloramphenicol was selected accordingly.

PCR was performed using the selected strain as a template and the same primers under the same conditions. The deletion of acs promoter and substitution of pro promoter were identified by confirming the 1.2 kb sized gene on 1.0% agarose gel. The strain was then transformed with pCP20 vector (PNAS (2000) vol. 97: 6640-6645) and cultured in LB medium. The final acs promoter deleted and pro promoter substituted strain was constructed in which the gene size was reduced to 150 bp on 1.0% agarose gel by PCR under the same experimental conditions, and it was confirmed that the chloramphenicol marker gene was deleted. The constructed strain was designated as CJM2-AP.

2-1-3) Substitution of Feedback Resistant coaA

In order to prepare CJM2-AP strain having feedback resistant coaA, PCR was performed using w3110 gDNA as a template and the primers of SEQ ID NO: 35 and SEQ ID NO: 36 containing the EcoRI restriction site so as to obtain a coaA gene encoding pantothenate kinase. High-fidelity DNA polymerase PfuUltra™ (Stratagene) was used as a polymerase, and PCR was performed under the conditions of 30 cycles consisting of denaturation at 96° C. for 30 seconds; annealing at 50° C. for 30 seconds; and polymerization at 72° C. for 2 minutes.

After treatment of the obtained coaA gene and pSG76C plasmid (Journal of Bacteriology, July 1997, 4426-4428) with the restriction enzyme EcoRI, they were ligated with each other. E. coli DH5α was transformed with the constructed plasmid, and then the transformed E. coli DH5α was selected on LB plate medium containing 25 μg/ml of chloramphenicol so as to obtain pSG-76C-coaA.

<SEQ ID NO: 35>
5' ATGAGTATAAAAGAGCAAAC 3'

<SEQ ID NO: 36>
5' TTATTTGCGTAGTCTGACC 3' pSG-76C-coaA (R106A) was constructed using the obtained pSG-76C-coaA and the primers of SEQ ID NO: 37 and SEQ ID NO: 38 by site directed mutagenesis (Stratagene, USA).

<SEQ ID NO: 37>
5' GGAAAAGTACAACCGCCgccGTATTGCAGGCGCTATT 3'

<SEQ ID NO: 38>
5' AATAGCGCCTGCAATACggcGGCGGTTGTACTTTTCC 3'

The CJM2-AP strain was transformed with the pSG76C-coaA (R106A) plasmid and cultured in LB-Cm (Yeast extract 10 g/L, NaCl 5 g/L, Tryptone 10 g/L, chloramphenicol 25 μg/L) medium to select chloramphenicol-resistant colonies. The selected transformant is a strain in which pSG76c-coaA (R106A) is primarily inserted into the coaA region of the genome.

The coaA (R106A) gene-inserted strain was transformed with a pASceP vector (Journal of Bacteriology, July 1997, 4426-4428) expressing the restriction enzyme I-SceI that cleaves the I-SceI site present in pSG76c, followed by selection of strains on LB-Ap (Yeast extract 10 g/L, NaCl 5 g/L, Tryptone 10 g/L, Ampicillin 100 μg/L). The coaA gene was amplified from the selected strain using the primers of SEQ ID NO: 35 and SEQ ID NO: 36, and the substitution of coaA (R106) in the amplified gene was confirmed by macrogen sequencing service (Korea) (Nucleic Acids Research, 1999, Vol. 27, No. 22 4409-4415). The prepared strain was designated as CJM2-AP/CO. The CJM2-AP/CO strain is a strain having increased homoserine and acetyl-coA pool.

2-1-4) Increase in Copy Number of Key Genes in Homoserine Biosynthetic Pathways Even though the CJM2 or CJM2-AP/CO strain is a strain producing an excessive amount of homoserine, the copy numbers of three genes of ppc, aspC, and asd were increased to more improve homoserine productivity. pSG76c-2ppc, pSG76c-2aspC, and pSG76c-2asd plasmids were constructed by the methods described in Examples <1-1> to <1-3> of Publication Patent No. KR2011-0023703, and the plasmids were introduced into the CJM2-AP/CO strain to prepare a strain having two copies of the three genes by the method of Example <1-5>. The prepared strain was designated as CJM3. CJM3 is a strain that accumulates a large amount of homoserine compared to the CJM2 strain, and produces O-acetyl homoserine or O-succinyl homoserine depending on the plasmid introduced.

2-2: Experimental Methods and Experimental Results

Two strains of CJM2 and CJM3 were prepared as competent cells, and 9 plasmids of pCL_Pcj1_metX, pCL_Pcj1_metA, pCL_Pcj1_metA(EL), pCL_Pcj1_metA (EH), pCL_Pcj1_metA(ET), pCL_Pcj1_metA#11, pCL_Pcj1_metA#11(EL), pCL_Pcj1_metA#11(EH), and pCL_Pcj1_metA#11(ET) were introduced into the competent cells by electroporation, respectively.

Among them, the CJM2 strains introduced with pCL_Pcj1_metA#11(EL), pCL_Pcj1_metA#11(EH), and pCL_Pcj1_metA#11(ET) were designated as CA05-0546, CA05-0547 and CA05-0548, respectively. They were deposited in the Korean Culture Center of Microorganism on Dec. 14, 2010, and assigned the accession numbers, KCCM11145P, KCCM11146P, and KCCM11147P, respectively.

Further, the CJM3 strains introduced with pCL_Pcj1_metA#11(EL), pCL_Pcj1_metA#11(EH), and pCL_Pcj1_metA#11(ET) were designated as CA05-0578, CA05-0579, and CA05-0580, respectively. They were deposited in the Korean Culture Center of Microorganism on Dec. 12, 2011, and assigned the accession numbers, KCCM11228P, KCCM11229P, and KCCM11230P, respectively.

Thereafter, a flask test was performed to compare the types and productivities of methionine precursors that were produced by each of the strains introduced with 9 types of plasmids. In the flask test, after streaking each strain on LB plates and culturing them in a 31° C. incubator for 16 hours, single colonies were inoculated in 3 ml of LB medium, and then cultured in a 200 rpm/31° C. incubator for 16 hours.

25 ml of the methionine precursor production medium of Table 1 was put in 250 ml flasks, and each 500 µl of the culture broths was added thereto. Then, the flasks were incubated in a 200 rpm/31° C. incubator for 40 hours, and the type and productivity of methionine precursor produced by each of the plasmid-introduced strains were compared by HPLC. The results are shown in Table 2 (results of CJM2-type strains) and Table 3 (results of CJM3-type strains).

TABLE 1

| Composition | Concentration (per liter) |
| --- | --- |
| Glucose | 70 g |
| Ammonium sulfate | 25 g |
| KH$_2$PO$_4$ | 1 g |
| MgSO$_4$•7H$_2$O | 0.5 g |
| FeSO$_4$•7H$_2$O | 5 mg |
| MnSO$_4$•8H$_2$O | 5 mg |
| ZnSO$_4$ | 5 mg |
| Calcium carbonate | 30 g |
| Yeast Extract | 2 g |
| Methionine | 0.3 g |
| Threonine | 1.5 g |

TABLE 2

| Strains | OD | Sugar consumption (g/L) | Product | Production amount (g/L) |
| --- | --- | --- | --- | --- |
| CJM2 pCL_Pcj1_metX | 35.6 | 63.8 | O-acetyl homoserine | 12.3 |
| CJM2 pCL_Pcj1_metA(wt) | 31.3 | 49.1 | O-succinyl homoserine | 2.7 |
| CJM2 pCL_Pcj1_metA EL | 32.6 | 48.3 | O-acetyl homoserine | 2.5 |
| CJM2 pCL_Pcj1_metA ET | 33.6 | 50.2 | O-acetyl homoserine | 2.0 |
| CJM2 pCL_Pcj1_metA EH | 31.9 | 47.5 | O-acetyl homoserine | 3.1 |
| CJM2 pCL_Pcj1_metA(#11) | 29.5 | 56.2 | O-succinyl homoserine | 11.3 |
| CJM2 pCL_Pcj1_metA(#11)EL | 32.7 | 49.0 | O-acetyl homoserine | 7.8 |
| CJM2 pCL_Pcj1_metA(#11)ET | 38 | 53.7 | O-acetyl homoserine | 6 |
| CJM2 pCL_Pcj1_metA(#11)EH | 34.5 | 59.1 | O-acetyl homoserine | 11.1 |

TABLE 3

| Strains | OD | Sugar consumption (g/L) | Product | Production amount (g/L) |
| --- | --- | --- | --- | --- |
| CJM3 pCL_Pcj1_metX | 17.2 | 67.0 | O-acetyl homoserine | 23.7 |
| CJM3 pCL_Pcj1_metA(wt) | 18.8 | 60.5 | O-succinyl homoserine | 1.2 |
| CJM3 pCL_Pcj1_metA EL | 18.5 | 60.5 | O-acetyl homoserine | 2.1 |
| CJM3 pCL_Pcj1_metA ET | 18.0 | 61.0 | O-acetyl homoserine | 2.2 |
| CJM3 pCL_Pcj1_metA EH | 17.8 | 62.2 | O-acetyl homoserine | 3.2 |
| CJM3 pCL_Pcj1_metA(#11) | 14.6 | 67.0 | O-succinyl homoserine | 16.1 |
| CJM3 pCL_Pcj1_metA(#11)EL | 17.1 | 63.2 | O-acetyl homoserine | 12.5 |
| CJM3 pCL_Pcj1_metA(#11)ET | 18.2 | 65.1 | O-acetyl homoserine | 16.7 |
| CJM3 pCL_Pcj1_metA(#11)EH | 19.0 | 67.8 | O-acetyl homoserine | 24.8 |

As shown in Tables 2 and 3, only O-succinyl homoserine was produced by pCL_Pcj1_metA(wt) including the wild-type metA gene, but only O-acetyl homoserine was accumulated by the strains including three mutated metA genes of the present invention. That is, homoserine succinyltransferase activity of the polypeptide was modified to homoserine acetyltransferase activity by substitution of its amino acids.

Further, among the three mutants of CJM3-type strain, the strain (EL) prepared by substitution of glutamic acid for the amino acid at position 111 produced 2.1 g/L of O-acetyl homoserine, whereas the strain (EH) prepared by additional substitution of histidine for the amino acid at position 112 produced 3.2 g/L of O-acetyl homoserine, which is the highest yield of O-acetyl homoserine.

The strains expressing modified polypeptides having homoserine acetyltransferase activity resistant to feedback regulation by methionine also showed the same results. Specifically, the metA #11(EH) gene-introduced strain, which had a resistance to feedback regulation by methionine and substitutions of glutamic acid and histidine for the amino acids at position 111 and 112, produced the largest amount of O-acetyl homoserine (24.8 g/L), indicating that it accumulates O-acetyl homoserine at the similar level to that introduced with the foreign homoserine acetyltransferase gene (CJM3 pCL_Pcj1_metX, 23.7 g/L).

Effect of the Invention

According to the present invention, O-acetyl homoserine can be produced from homoserine without introduction of a foreign gene into a microorganism that expresses an enzyme which converts homoserine into O-succinyl homoserine, and the above O-acetyl homoserine can be used as a precursor for the production of methionine. Therefore, when the present invention is applied to the production of methionine for use in foods, it is advantageous in that the problems of anxiety and negative attitudes of consumers toward introduction of foreign genes and provision of proof of safety for the introduction of foreign genes can be solved.

What is claimed is:

1. A polypeptide having homoserine O-acetyltransferase activity that is at least 95% homologous to the amino acid sequence of SEQ ID NO: 17, wherein the amino acid at position 111 from the start amino acid methionine of the sequence is substituted with glutamic acid, and the amino acid at position 112 of the sequence is substituted with threonine or histidine.

2. A polypeptide having homoserine O-acetyltransferase activity that is at least 95% homologous to the amino acid sequence of SEQ ID NO: 17, wherein
the amino acid at position 111 from the start amino acid methionine of the sequence is substituted with glutamic acid,
the amino acid sequence is further substituted with proline at position 29, substituted with glycine at position 114, substituted with serine at position 140, or one or more combinations of them, and
the amino acid sequence is further substituted with threonine or histidine at position 112.

3. The polypeptide according to claim 2, wherein the polypeptide exhibits resistance to feedback regulation by methionine.

4. A polypeptide having homoserine O-acetyltransferase activity that is at least 95% homologous to the amino acid sequence of SEQ ID NO: 17, wherein
the amino acid at position 111 from the start amino acid methionine of the sequence is substituted with glutamic acid,
the amino acid sequence is further substituted with proline at position 29, substituted with glycine at position 114, substituted with serine at position 140, or one or more combinations of them, and
the polypeptide exhibits resistance to feedback regulation by methionine, and has the amino acid sequence of SEQ ID NO: 21.

5. A polynucleotide encoding the polypeptide of claim 1.

6. The polynucleotide according to claim 5, wherein the polynucleotide has any one of the nucleotide sequences of SEQ ID NOs: 25, 26, 28 and 29.

7. A recombinant vector comprising polynucleotide sequences operably linked to the polynucleotide of claim 5.

8. A microorganism comprising the polynucleotide of claim 5.

9. The microorganism according to claim 8, wherein the microorganism is additionally modified to have enhanced acetyl-CoA synthetase activity compared to the endogenous acetyl-CoA synthetase activity by introduction of an activity enhanced promoter, substitution of the native promoter of acetyl-CoA synthetase with a pro promoter, or increasing the copy number of the nucleic acid encoding acetyl-CoA synthetase, or additionally modified to have pantothenate kinase activity resistant to feedback inhibition by CoA accumulation by substituting an amino acid at a position of the pantothenate kinase of the microorganism which corresponds to position 106 of SEQ ID NO. 40 with alanine.

10. The microorganism according to claim 8, wherein the copy number of one or more coding sequences selected from the group consisting of coding sequence for phosphoenolpyruvate carboxylase (ppc), coding sequence for aspartate aminotransferase (aspC), and coding sequence for aspartate semialdehyde dehydrogenase (asd) is increased, or the promoter of the coding sequence is replaced by an activity-enhanced promoter.

11. A microorganism transformed with the recombinant vector of claim 7.

12. The microorganism according to claim 11, wherein the microorganism belongs to the genus *Escherichia*.

13. The microorganism according to claim 12, wherein the microorganism is *E. coli*.

14. The microorganism according to claim 13, wherein the microorganism is deposited under accession number of KCCM11146P, KCCM11147P, KCCM11229P or KCCM11230P.

15. A method for producing O-acetyl homoserine, comprising culturing the microorganism of claim 8; and obtaining O-acetyl homoserine that is produced during cultivation of the microorganism.

16. The polypeptide according to claim 1, wherein the polypeptide has the amino acid sequence of SEQ ID NO: 19 or 20.

17. The polypeptide according to claim 5, wherein the polypeptide has the amino acid sequence of SEQ ID NO: 22 or 23.

18. A polynucleotide encoding the polypeptide of claim 2.

19. A recombinant vector comprising polynucleotide sequences operably linked to the polynucleotide of claim 18.

20. A microorganism comprising the polynucleotide of claim 18.

21. A microorganism transformed with the recombinant vector of claim 19.

22. The microorganism according to claim 21, wherein the microorganism is *E. coli*.

23. The microorganism according to claim 22, wherein the microorganism is deposited under accession number of KCCM11145P or KCCM11228P.

* * * * *